(12) United States Patent
Clifford, III et al.

(10) Patent No.: US 7,871,525 B2
(45) Date of Patent: Jan. 18, 2011

(54) BIOMASS TREATMENT OF ORGANIC WASTE OR WASTE WATER

(75) Inventors: Robert E. Clifford, III, Minnetonka, MN (US); John Mills, Shoreview, MN (US); Greg Stadden, Golden Valley, MN (US); Michael S. Gratz, Eden Prairie, MN (US)

(73) Assignee: NBE, LLC, Eden Prairie, MN (US)

( * ) Notice: Subject to any disclaimer, the term of this patent is extended or adjusted under 35 U.S.C. 154(b) by 0 days.

(21) Appl. No.: 12/316,348

(22) Filed: Dec. 11, 2008

(65) Prior Publication Data

US 2009/0261037 A1 Oct. 22, 2009

Related U.S. Application Data (63) Continuation of application No. 11/506,394, filed on Aug. 18, 2006, now Pat. No. 7,481,940.

(60) Provisional application No. 60/709,313, filed on Aug. 18, 2005.

(51) Int. Cl.
*C02F 3/00* (2006.01)

(52) U.S. Cl. .................. 210/739; 210/740; 210/741; 210/742; 210/743; 210/744; 210/745; 210/746

(58) Field of Classification Search .......... 210/739–746
See application file for complete search history.

(56) References Cited

U.S. PATENT DOCUMENTS

| 7,422,692 B1* | 9/2008 | Sanders ...................... 210/709 |
| 2001/0040102 A1* | 11/2001 | Hu et al. .................... 205/754 |

* cited by examiner

*Primary Examiner*—Chester T Barry
(74) *Attorney, Agent, or Firm*—Mark A Litman & Associates PA (57) ABSTRACT

A method, system, apparatus and program for effecting the decomposition of organic waste material comprises: providing a treatment tank for decomposition of organic waste material, the treatment tank containing an active biomass comprising at least one bacteria that decomposes organic material; providing at least two inlets to the treatment tank, a first inlet comprising an inlet for organic material and a second inlet comprising an inlet for an aqueous stream; a processor that receives and stores information on: the status of chemical oxygen demand of the active biomass; and the oxygen provision capability of a first organic material that can be fed into the treatment tank through the first inlet; a mass flow control system controlled by the processor which feeds the at least one organic material through the first inlet at a rate based at least in part upon the status of chemical oxygen demand in the treatment tank as recognized by the processor.

12 Claims, 1 Drawing Sheet

FIG. 1

BIOMASS TREATMENT OF ORGANIC WASTE OR WASTE WATER

RELATED APPLICATION DATA

This application is a continuation of U.S. patent application Ser. No. 11/506,394, filed Aug. 18, 2006, now U.S. Pat. No. 7,481,940, which in turn claims priority from Provisional application 60/709,313 filed 18 Aug. 2005.

BACKGROUND OF THE INVENTION

1. Field of the Invention

The present invention relates to the field of material wastes, organic contaminants, water waste, and organic waste, and the conversion of such waste and contaminants to easily disposed materials by using biomass treatment, such as active or bacterial biomass to convert organic materials into primarily gaseous waste products.

2. Background of the Art

The safe disposal of waste or contaminating materials has been recognized as a significant health and economic issue for many years. The ability to merely dump raw materials into the oceans or landfill materials is no longer an acceptable mechanism for disposal. Not only do landfills face a limitation on space and require significant energy to transport and deposit materials, but they are recognized as either potential health hazards and ecologically destructive of their locations and adjacent land areas, especially because of underground seepage of materials. It has therefore become recognized that methods of disposal, especially or organic materials, must convert the materials to more readily tolerated products, whether solid, liquid or gaseous in final form. Certain technology has used collection of natural gas decomposition product collection from landfills to more efficiently use landfills, and this is an economic benefit, but still requires the use of new or existing landfills and does not reduce the volume of solids that must be landfilled. Incineration of materials has also come into disfavor because of the emission of gases directly into the environment, and even after scrubbing, noxious or even toxic materials (in addition to volumes of carbon dioxide) are undesirably emitted into the atmosphere.

One system that has been developed to assist in the conversion and disposal of organic waste materials is referred to as the active biomass conversion process in which organic materials are fed to an active, bacterial mass that digests the organic materials and converts them into gaseous wastes that may be collected or more easily and safely disposed of than are solid and concentrated liquid products.

U.S. Pat. No. 6,821,425 (US EPA) describes a biomass concentrator reactor as a gravity flow-through system, as opposed to a conventional pressure or vacuum system. The advantage of the biomass concentrator reactor of the present invention is the use of gravity flow, which makes possible operational simplicity and significantly reduced operation and maintenance costs. The capital cost of equipment is very low because there is no need for pressurization. Biological treatment of any contaminated liquid stream is greatly facilitated by maintenance of a long sludge age and retention of a high biomass solids content.

The patent utilizes a gravity-flow biomass concentrator reactor comprising an intake for water to be treated, said intake leading into a housing enclosing at least one porous barrier having pore sizes such that water permeates through the porous barrier under the pressure of gravity, said porous barrier comprising an aggregate of polyethylene beads, and wherein substantially all suspended solids in the water are retained by the barrier, and an outflow from the housing through which treated water flows. The porous barrier has pore sizes ranging from about 1 to about 50 microns.

U.S. Pat. No. 6,838,000 (Braun) describes an activated sludge tank (7b) which allows the necessary concentration of active bio mass in the oxidation apparatus to be appropriately adjusted depending on the day profile of the amounts and loads of the accruing black water in conjunction with an oxygen supply adjusted to the demand (7c), in order to ensure a constant drainage quality. This leads to a substantially smaller dimensioning of the reaction volumina and a more stable course of the process compared to that of the prior art. The process can be computer-controlled and/or can be DFU- (remote data transmission)-controlled. Operation can be monitored by sensors. The demand-dependent and controllable bio mass concentration in the oxidation apparatus could have an influence on the special requirements of the process of the invention. For instance, the sharp rises in acidity and/or the accumulation of $HNO_2^{-N}$ in the oxidation apparatus could be counteracted by an appropriate supply of active bio mass and/or Nitrobacter-enriched bio mass from the activated sludge tank. This also enables the plant when adequately controlled to adapt to the day profile of loads even in the case of the smallest reactor dimension. The patent specifically describes a method of treating sewage which reduces nitrogen concentrations in, and the size of, bio gas plants; said method comprising: separately collecting black water; selectively performing liquid/solid separation of said black water by membrane filtration; and performing anaerobic fermentation of solids of said black water.

The following patents provide a narrower view of wastewater treatment systems with nutrients for bacterial digestion of sold matter, and each is incorporated by reference for its disclosure of bacteria, methods, apparatus, components and materials: U.S. Pat. Nos. 6,863,826; 6,846,343; 6,838,000; 6,797,500; 6,737,020; 6,719,903; 6,682,578; 6,660,164; 6,632,650; 6,630,197; 6,630,067; 6,514,411; 6,508,078; 6,503,746; 6,398,959; 6,383,389; 6,342,378; 6,203,701; 6,197,081; 6,190,566; 6,168,717, and the like.

U.S. Pat. No. 6,719,903 discloses a major benefit of a control scheme comprising an ORP (oxygen reduction potential) sensor inventive control scheme is energy efficiency. The control scheme supplies the required horsepower to increase oxygen supply when necessary and conserves energy when the demand is lower. Another extremely important advantage of this control scheme is that it may prevent sulfur compounds from reducing and producing unwanted and very foul odors in addition to keeping the production of unwanted volatile fatty acids to a minimum. The process is for the aerobic treatment in a biosolids treatment reactor of a biosolids solution comprising the products of waste water treatment and thermophilic bacteria capable of digesting mesophilic bacteria. The process comprises: (a) mixing a portion of the biosolids solution with an oxygen-containing gas stream using a jet aeration device; (b) monitoring at least one physical property indicative of oxygen demand of the biosolids solution; (c) adjusting the mixing of biosolids solution with the oxygen-containing gas stream by the jet-aeration device such that sufficient oxygen is supplied to satisfy oxygen demand, wherein the monitoring step comprises monitoring the temperature and the oxygen/reduction potential of the biosolids solution.

U.S. Pat. Nos. 6,660,164 and 6,036,862 describe only that if the ORP (oxygen reduction potential) is allowed to reduce enough to allow anaerobic bacteria to thrive, sulfides can be produced from wastes containing sulfates and/or organic sulfur containing compounds. This will yield sulfides in the bulk liquid. Hydrogen sulfide ($H_2S$) is partially soluble and insoluble, and as the $H_2S$ is produced above its solubility level, it diffuses out of solution and into the offgas. This is a normal aspect of anaerobic systems and the amount of sulfides in the bulk liquid and $H_2S$ in the biogas must be monitored and controlled to achieve maximum treatment performance. The sulfides level in the reactor bulk liquid is determined using wet chemistry techniques, while the $H_2S$ level in the offgas is determined using the $H_2S$ sensor 176.

U.S. Pat. No. 6,203,701 similarly describes that a major benefit of a control scheme comprising an ORP sensor inventive control scheme is energy efficiency. The control scheme supplies the required horsepower to increase oxygen supply when necessary and conserves energy when the demand is lower. Another extremely important advantage of this control scheme is that it may prevent sulfur compounds from reducing and producing unwanted and very foul odors in addition to keeping the production of unwanted volatile fatty acids to a minimum.

These systems have minimum automated controls and are deficient in their ability to handle multiple sources of organic products.

SUMMARY OF THE INVENTION

The disclosed technology relates to the field of waste management and particularly waste disposal and reuse of waste materials. The present disclosure includes at least software, apparatus, processes and business methods for the implementation of this technology. A method of decomposition of organic waste material practiced on the apparatus and using the software described herein ma, by way of non-limiting examples, comprise:

providing a treatment tank for decomposition of organic waste material, the treatment tank containing an active biomass comprising at least one bacteria that decomposes organic material;

providing at least two inlets to the treatment tank, a first inlet comprising an inlet for organic material and a second inlet comprising an inlet for an aqueous stream;

a processor that receives and stores information on:

the status of chemical oxygen demand of the active biomass; and the oxygen provision capability of a first organic material that can be fed into the treatment tank through the first inlet;

a mass flow control system controlled by the processor which feeds the at least one organic material through the first inlet at a rate based at least in part upon the status of chemical oxygen demand in the treatment tank as recognized by the processor.

DETAILED DESCRIPTION OF THE INVENTION

It is to be noted that the treatments processes of the technology described herein should be directed primarily at organic waste treatment, which may come from a wide variety of sources. Preferred organic materials come from more readily definable and consistent composition waste sources such as industrial, commercial, and recycled wastes. This assists in assuring that materials are present that are not treated by the biomass or should not be introduced into the biomass, such as metals (even in high concentrations in dissolved or organically tied or chelated form), toxins (especially materials that would be toxic to bacteria, such as pesticides), and non-digestible materials that would tend to collect in the biomass without digestion or decomposition. It is possible to provide a venting/discharge system for such non-digestible materials, but as noted, it is preferred to avoid introduction of significant amounts (e.g., greater than 0.5%, greater than 0.2%, or greater than 0.05% by total solids weight) into the system. It is desirable to understand the basic terminology and activity within a treatment system of the general type described herein, and the immediately following discussion is intended to assist in an appreciation of that technology. Anaerobic digestion is the biological degradation of organic material without oxygen present. This results in the production of biogas, a valuable (energy containing) product.

Biogas produced from the treatment processes described herein usually comprises a mixture of several gases and vapors, mainly methane and carbon dioxide, although by selection of bacteria and particular biomass feed materials, hydrogen and other useful gases may be provided. Methane is the main component in natural gas and contains the bulk energy value of the biogas, with the exception of hydrogen gas, which may be useful either for fuel cell energy production or direct combustion. Biogas occurs naturally, hence its name, amongst others in swamps and lakes when conditions are right. Anaerobic digestion within the systems and processes described herein can be used to produce valuable energy from waste streams of natural materials or to lower the pollution potential of a waste stream. The system is generally described as a biological system, indicating that the process is carried out by biological actives such as bacteria. The bacteria in the active or digestive biomass have to be kept healthy while sustaining conditions for the bacteria. The bacteria degrade or digest or decompose the organic matter fed into the system. This means that the organic material is broken down into component parts or converted (by digestion) into biogas. The system is generally operated in an anaerobic environment, without oxygen. This means that air is not allowed to directly interact with the organic materials as they are being digested. To promote the production of biogas as a valuable product of the degradation, oxygen should or must be kept away from the environment where the biomass is decomposing the organic materials.

There may be a number of steps that occur in the bacterial anaerobic degradation of the organic materials. These steps may include at least some of the following: 1. hydrolysis: high weight organic molecules (like proteins, carbohydrates, fat, cellulosis) are broken down into smaller molecules like sugars, amino acids, fatty acids and water. 2. acidogenesis: further breakdown of these smaller molecules into organic acids, carbon dioxide, hydrogen sulfide and ammonia occurs. 3. acetagenesis: the products from the acidogenesis are used for the production of acetates, carbon dioxide and hydrogen. 4. methanogenesis: methane (finally), carbon dioxide and water are produced from the acetates, carbon dioxide and hydrogen (products of acidogenesis and acetagenesis). 5. There are several groups of bacteria that perform each step; in total dozens of different species are needed to degrade a heterogeneous stream completely.

Process Parameters

The anaerobic digestion process can be carried out quite different conditions. All of these conditions have specific influences on the biogas production. Additionally, from a technological viewpoint, the biological process can also be carried out in more than one reactor, which has some, mainly economical, implications.

"Dry" Digestion Vs "Wet" Digestion

In digestion processes, water is an important parameter. Water is needed for life in general and for digestion bacteria, too. It is the transport medium for nutrients, for (half-) products and it is a very good reaction medium for digestion.

Digestion is practiced in two different ranges of water content: dry digestion, with a typical dry solids content of 25-30% and wet digestion, with a dry solids content of less than 15%. These ranges have technological and economic reasons: higher solid contents lead to smaller (and thus cheaper?) reactors, lower solids contents (more water) lead to much better mixing possibilities but to a higher energy input (more water to be heated) and a bigger reactor.

Natural wastes from plants (like greenhouse residues) have an estimated dry solids content of 25%. This dry solids content opens the possibility to perform the digestion without addition of water.

Thermophilic Vs Mesophilic Digestion (Digestion) bacteria have a temperature range in which they are most productive in terms of production rates, growth rates and substrate degradation performance. The several groups of bacteria involved in anaerobic digestion all have (slightly) different temperature optimums. This results in two main temperature ranges in which digestion usually can be performed optimally and most economically. These ranges are: 25-38° C. called the mesophilic range, and 50-70° C. called the thermophilic range.

These ranges have different characteristics, advantages and disadvantages of which the most important ones are: compared to the mesophilic process, the thermophilic process usually results in a higher degradation of the substrate at a faster rate at the expense of a less stable process. It is less attractive from an energetic point of view since more heat is needed for the process.

Batch Processes Vs Continuous Processes

In process technology the two main types of process models are used, the batch process and the continuous process. In the batch process the substrate is put in the reactor at the beginning of the degradation period after which the reactor is closed for the entire period without adding additional substrate. In the continuous process, the reactor is filled continuously with fresh material and also emptied continuously.

As explained before, digestion consists of several consecutive steps. In a batch reactor all these reaction steps occur more or less after each other. The production of biogas (endproduct) is non-continuous: at the beginning only fresh material is available and the biogas production will be low. Halfway through the degradation period the production rate will be highest and at the end, when only the less easily digestible material is left, production rate will drop again.

In a continuous process, fresh substrate is added continuously, and therefore all reactions will occur at a fairly constant rate resulting in a fairly constant biogas production rate. Several mix forms of these two models are developed in process technology including the so-called plug-flow reactor and the sequencing batch-reactor all of which try to combine the advantages of the two extremes.

Residence Time

The longer a substrate is kept under proper reaction conditions the more complete its degradation will become. But the reaction rate will decrease with increasing residence time. The disadvantage of a longer retention time is the increasing reactor size needed for a given amount of substrate to be treated. A shorter retention time will lead to a higher production rate per reactor volume unit, but a lower overall degradation. These two effects have to be balanced in the design of the full scale reactor.

Acidity or pH-Value

The groups of bacteria needed for digestion not only have an optimum temperature but also an optimum acidity at which they are most productive. Unfortunately, for the different groups of bacteria the optimum pH-value (measure for acidity) is not the same. The complexity of the entire system is increased by the fact that the intermediate products of the digestion have a tendency to lower the pH, making the later steps in the process more difficult. This makes balancing the pH in the reactor an important design and operation issue.

Organic Loading

Bacteria have a maximum production rate depending on the type of reactor, substrate, temperature etc. Organic loading is one of parameters used to describe this production rate. It is the amount of organic material put into the reaction medium per time unit.

The underlying area of technology may involve a water-based input stream into the system, a biomass or organic mass input feed stream into the system, an approximately steady or growing biomass within the system, a gaseous output stream, a liquid output stream (water-based), and an incidental (or optional) active biomass control activity. Each of the streams will be discussed. The term stream is used in the Chemical Engineering sense in that it represents a mass input, but the term stream is not limited to a continuous flow input, but includes an episodic/periodic or batch input or output.

The water-based input stream (which is desirable for ultimately sustaining a water-based output stream and assisting in the removal of soluble, suspendable, dispersible or otherwise carriable waste materials from the system) may be a potable input stream (either naturally source of water, such as a stream, lake, river, etc., or purified supply as from a treatment plant or well) or may be a waste stream containing dissolved, suspended, dispersed or otherwise carried organic materials, and preferably little content (e.g., less than 0.5% by weight or volume) that cannot be digested by bacteria in the active biomass, as indicated above. Industrial waste water streams may be desirable, especially where the organic and other content of the stream can be anticipated or even controlled, and will exclude those types of materials that are incompatible with a biomass treatment system, also as indicated above. Such streams might be from food processing plants, pharmaceutical plants, and the like. Streams containing animal waste products are not preferred. By accessing such water waste streams, low cost water that can itself be treated for ease of disposal can be used, as opposed to using potable water streams.

The organic feed stream (in addition to any organic materials that are carried in the water-based feed stream) may include any organic materials that can be digested by bacteria, such as dated food products (e.g., cheese, cheese by-products, processed cheese, low cellulosic content vegetable and fruit masses (e.g., preferably excluding wood products having significant persistent or non-digestible cellulose material) such as rice starch, potato starch, potato mass, wheat starch, sugars, syrups, animal waste products (excluding bone and certain non-digestible tissue, such as cartilage), synthetic organic materials, natural organic materials, dairy products or dairy intermediates in general (e.g., yogurt, ice cream, milk, milk fat, cream, egg content preferably excluding shells), baked goods, expired food products, and the like.

Biomass content is designed to assist in treatment, digestion, decomposition of the anticipated content of the organic biomass feed stream. Sources of such bacteria, any required nutrients, and the like can be found commercially, as for example, from BZT® Waste Digester cultures, enzymes and nutrients used to improve biotreatment performance and reduce BOD/COD (biochemical oxygen demand/chemical oxygen demand) loads in municipal and industrial water treatment clarifiers, trickling filters, ponds, lagoons, activated sludge systems and aerobic and anaerobic digesters. Amnite™ L100 systems from Cleveland Biotech LTD are another source of microorganisms. Other sources of biomass and supplements include Bionetix® Canada systems, Specific types of bacteria for such processes include, but are not limited to Bacteria; Proteobacteria; Alphaproteobacteria; Rhizobiales; Bradyrhizobiaceae, including such specific species as *Rhodopseudomonas cryptolactis; Rhodopseudomonas faecalis; Rhodopseudomonas julia; Rhodopseudomonas palustris; Rhodopseudomonas rhenobacensis*; and *Rhodopseudomonas sp.* Even though, as indicated above, wood and high cellulosic content materials are not preferred, *R. palustris* has the potential to be very useful because it can degrade and recycle several different aromatic compounds that make up lignin, the main constituent of wood and the second most abundant polymer on earth. Thus, this bacterium and those like it may be useful in removing these types of waste from the environment. In addition, *R. palustris* converts $NH_4$ into $N_2$ and $H_2$, which can be used as a biofuel. *Chlamydomonas reinhardtii* has been found to be effective in the production of hydrogen gas from certain organic mass sources.

The emission streams basically comprise a water-based output stream, the gaseous emission stream, and the potentially periodic biomass output stream. The gaseous emission stream comprises the gaseous decomposition or digestion products made by the active or bacterial biomass on the organic mass input stream. The primary gases (depending upon the particular bacteria and organic mass feed provided) comprise gases selected from the group consisting of carbon dioxide, methane, hydrogen, ammonia, hydrogen sulfide, and the like.

The water based output stream comprises water and dissolved, suspended, dispersed or otherwise carried organic matter. The water output stream can be in sufficiently acceptable form as to be sent directly to standard (e.g., municipal) water treatment facilities for conversion to potable or at least agriculturally useful water.

The biomass output can be little more than removal of biomass after growth of the biomass (the microorganisms) has exceeded a volume that is useful within the digestion/treatment/decomposition environment or tank or reactor. The biomass is then removed and may be treated for direct use (e.g., fertilizer) or transported to another treatment facility to become starter, replenishment, or enhancing biomass for another treatment facility. There are certain biomass system bacteria that are known as non-growth bacteria that can be useful in the present technology, which would avoid the need for any regular removal of biomass as a stream. At the present time, those tend to be more expensive, less active, and are therefore not preferred. The provision of another commercial product in the biomass solids is also a benefit to the economics of the system.

An important additional aspect of the presently described system is the automation of controls to the system. Multiple organic mass inputs may be provided (e.g., in batch deposits, or by more controlled batch input from holding or storage tanks). As the content of the organic materials can be determined in advance of their introduction into a reaction vessel, and as the content or rate of addition of various materials can and should be controlled, and as the conditions and content of the reaction vessel can be monitored, automated controls can be provided in the present system to provide more frequent and more reliable control over the performance of the system. For example, even as organic input stream material is stored, its content and characteristics can change, so that merely providing a single input consideration of the material into the reaction controls and stoichiometry of the treatment process can lead to wide variations in system output. As the systems are intended to produce a marketable or immediately useful energy product (methane and/or hydrogen) and commercial gas stream (e.g., carbon dioxide), it is essential that the system be provided with control sufficient to assure a reliable output of the intended gaseous products.

Sensing of parameters and conditions and properties within the system (defined as any and all of including input streams, output streams, and reaction vessels) can provide information or data that can be interpreted by or responded to by artificial intelligence (e.g., processors, hardware, software, field programmable gated arrays (FPGA), ASICS, chips, and the like) to alter mass flow, temperature, reaction times, pH, pressure, nutrient addition, and the like. Among some of the types of particular analysis or sensing are estimated chemical oxygen demand (COD), estimated Biochemical Oxygen Demand (BOD), pH at various locations within the system, temperature at various locations within the system, pressure at various points within the system, specific chemical content at various points within the system, mass flow rates (including solids, liquids and gases), nutrient requirements and estimates, and the like. The following discussions relate to the software aspects of at least some of these areas of the system that can and should be regulated by processed or automated control.

The software will operate an anaerobic digestion wastewater treatment system. The treatment system consists of multiple tanks, pumps and process instrumentation. The process may begin with influent raw wastewater being pumped into an equalization tank. From the equalization tank, the water is pumped to the anaerobic digester. The treated water flows from the digester, through the gas separation tank to final discharge. There is gas generated from the treatment process that is discharged to the flare or to other process equipment. The equalization tank (EQ Tank) is used to store the raw wastewater being pumped to the treatment system. The EQ Tank contains an internal mixer to ensure thorough mixing of the raw wastewater before it is pumped into the digester. There is also chemical (base) addition to the EQ Tank to maintain a neutral pH. Multiple process instruments are associated with the equalization tank to monitor the raw wastewater including liquid level, pH and temperature. Inside the anaerobic digester, there is biomass used to treat the wastewater. There is also an internal sand filter, used to filter the effluent water, maintained by two rotating arms. There are multiple process instruments associated with the digester to monitor the water and gas. These include liquid level, pH, temperature, arm position, pressure and gas concentration.

All of the process instrumentation and equipment may be connected to a programmable logic controller (PLC) or other logic system (which includes distributed architecture as opposed to an exclusively central control used with most PLC systems), which controls the operation of the treatment system.

Process Systems with Related Software Routines

For each element of the digestion process there may be numerous process systems. The process systems of the anaerobic digestion wastewater treatment system are each operated by a software routine. The elements of the digestion process and the related process systems are:

Equalization (Eq) System
    EQ Feed Pump and Valve Control
    EQ Tank Chemical Addition Pump Control
    EQ Mixer Speed Control
    EQ Feed Pump VFD Fault alarm
    EQ Mixer VFD Fault alarm
    EQ Tank Liquid Temperature alarms
    EQ Tank Liquid Level alarms
    EQ Tank Feed Pump Current alarms
    EQ Tank Mixer Current alarms
    EQ Tank pH alarms Digester Feed System
    Digester Feed Pump and Valve Continuous Control
    Digester Feed Pump and Valve Batch Control
    Digester Feed Pump Flow totalization
    Digester Liquid Level alarms
    Digester Foam Level High alarm
    Digester Feed Pump Current alarms
    Digester Feed Pump VFD Fault alarm
    Digester Liquid Level Transducer Error alarm Digester Agitation System
    Normal Fluidization Control
    Deep Clean Fluidization Control
    Sludge Rake Blade Pump Current alarms
    Sand Fluidization Blade Pump Current alarms
    Sludge Rake Blade Pump Pressure alarms
    Sand Fluidization Blade Pump Pressure alarms
    Sludge Rake Blade Pump VFD Fault alarm
    Sand Fluidization Blade Pump VFD Fault alarm Digester Discharge Control System
    Digester Discharge Valve Control
    Digester Effluent Flow Totalization
    Gas Separation Tank Liquid Level High alarm Gas Handling System
    Foam Lockout Control
    Gas Analyzer Drain Control
    Gas Pressure High alarm
    Gas Temperature Low alarm Digester Temperature Control System
    Digester Liquid Temperature Control
    Digester Liquid Temperature High and Low alarms Chemical Addition System
    Chemical Recirculation Pump Control
    Digester Liquid pH High and Low alarms
    Chemical Recirculation Pump Liquid Pressure High and Low alarms
    Chemical Recirculation Pump VFD Fault alarm
    Base Addition Pump Control
    Metal Addition Pump Control
    Nutrient Addition Pump Control
    Sulfur Addition Pump Control
    Anti-Foam Pump Control Other On-Line Instruments
    System Air Pressure Low alarm
    Titration System

| Operator Adjustable Process Set Points | Operator Adjustable Alarm Set Points | System Alarms |
| --- | --- | --- |
| EQ Tank Feed Pump ON Liquid Level | | EQ Tank Liquid Level High-High |
| EQ Tank Feed Pump OFF Liquid Level | | EQ Tank Liquid Level Low-Low |
| EQ Tank Feed Pump VFD Continuous Mode Speed | EQ Tank pH High | EQ Tank pH High |
| EQ Tank Feed Pump VFD Maximum Speed | EQ Tank pH Low | EQ Tank pH Low |
| EQ Tank Feed Pump VFD Minimum Speed | EQ Tank Temperature High | EQ Tank Temperature High |
| EQ Tank Feed Pump Daily Gallons | EQ Tank Temperature Low | EQ Tank Temperature Low |
| EQ Tank Mixer VFD Continuous Mode Speed | EQ Tank Feed Pump Current High | EQ Tank Feed Pump Current High |
| EQ Tank Mixer VFD Maximum Speed | EQ Tank Feed Pump Current Low | EQ Tank Feed Pump Current Low |
| EQ Tank Mixer VFD Minimum Speed | EQ Tank Feed Pump Pressure High | EQ Tank Feed Pump Pressure High |
| EQ Tank Mixer VFD Maximum Speed Liquid Level | EQ Tank Feed Pump Pressure Low | EQ Tank Feed Pump Pressure Low |
| EQ Tank Mixer VFD Minimum Speed Liquid Level | EQ Tank Feed Pump Flow Low | EQ Tank Feed Pump Flow Low |
| EQ Tank Mixer Intermittent Mode On Time | | EQ Tank Feed Pump VFD Fault |
| EQ Tank Mixer Intermittent Mode Off Time | EQ Tank Mixer Current High | EQ Tank Mixer Current High |
| EQ Tank Mixer Before Feed On Time | EQ Tank Mixer Current Low | EQ Tank Mixer Current Low |
| EQ Tank pH | | EQ Tank Mixer VFD Fault |
| EQ Tank pH Variation | Digester Liquid Level High | Digester Liquid Level High |
| Digester Feed Pump On Liquid Level | Digester Liquid Low | Digester Liquid Low |
| Digester Feed Pump Off Liquid Level | | Digester Liquid Level High-High |
| Digester Feed Pump VFD Continuous Mode Speed | | Digester Liquid Low-Low |
| Digester Feed Pump VFD Maximum Speed | Digester pH High | Digester pH High |
| Digester Feed Pump VFD Minimum Speed | Digester pH Low | Digester pH Low |
| Digester Feed Pump Daily Gallons | Digester Temperature High | Digester Temperature High |
| Digester Base Addition High pH | Digester Temperature Low | Digester Temperature Low |
| Digester Base Addition Low pH | Digester Feed Pump Current High | Digester Feed Pump Current High |
| Rake Blade Pump VFD Continuous Mode Speed (Rake Mode) | Digester Feed Pump Current Low | Digester Feed Pump Current Low |
| Rake Blade Pump VFD Maximum Speed (Rake Mode) | Digester Feed Pump Pressure High | Digester Feed Pump Pressure High |
| Rake Blade Pump VFD Minimum Speed (Rake Mode) | Digester Feed Pump Pressure Low | Digester Feed Pump Pressure Low |
| Rake Blade Pump VFD Initial Speed (Propulsion Mode - Normal Fluidize) | Digester Feed Pump Flow Low | Digester Feed Pump Flow Low |
| Rake Blade Pump VFD Initial Speed (Propulsion Mode - Deep Clean Fluidize) | Digester Liquid Level Transducer Allowable Difference | Digester Liquid Level Transducer Error |
| Rake Blade Pump VFD Maximum Speed (Propulsion Mode) | Digester Gas Pressure High | Digester Gas Pressure High |
| Rake Blade Pump VFD Minimum Speed (Propulsion Mode) | Rake Blade Pump Current High | Rake Blade Pump Current High |
| Rake Pump Intermittent Mode On Time | Rake Blade Pump Current Low | Rake Blade Pump Current Low |
| Rake Pump Intermittent Mode Off Time | Rake Blade Pump (Rake Mode) Pressure High | Rake Blade Pump (Rake Mode) Pressure High |
| Rake Blade RPM | Rake Blade Pump (Rake Mode) Pressure Low | Rake Blade Pump (Rake Mode) Pressure Low |

-continued

| Operator Adjustable Process Set Points | Operator Adjustable Alarm Set Points | System Alarms |
|---|---|---|
| Fluidization Blade (Normal Fluidize) RPM | Rake Blade Pump (Propulsion Mode) Pressure High | Rake Blade Pump (Propulsion Mode) Pressure High |
| Fluidization Blade (Deep Clean Fluidize) RPM | Rake Blade Pump (Propulsion Mode) Pressure Low | Rake Blade Pump (Propulsion Mode) Pressure Low |
| Fluidization Blade Pump VFD Initial Speed | Fluidization Blade Pump Pressure High | Fluidization Blade Pump Pressure High |
| Fluidization Blade Pump VFD Maximum Speed | Fluidization Blade Pump Pressure Low | Fluidization Blade Pump Pressure Low |
| Fluidization Blade Pump VFD Minimum Speed | Fluidization Blade Pump Current High | Fluidization Blade Pump Current High |
| Chemical Feed Pump VFD Initial Speed | Fluidization Blade Pump Current Low | Fluidization Blade Pump Current Low |
| Chemical Feed Pump VFD Maximum Speed | Chemical Feed Pump Pressure High | Chemical Feed Pump Pressure High |
| Chemical Feed Pump VFD Minimum Speed | Chemical Feed Pump Pressure Low | Chemical Feed Pump Pressure Low |
| Normal Fluidization - Time to Complete | Chemical Feed Pump Current High | Chemical Feed Pump Current High |
| Normal Fluidization - Number of Clicks to Complete | Chemical Feed Pump Current Low | Chemical Feed Pump Current Low |
| Deep Clean Fluidization - Time to Complete | | |
| Deep Clean Fluidization - Number of Clicks to Complete | | |
| Deep Clean Fluidization - Number of failed normal fluidizes to start deep clean | | |
| Digester Discharge Liquid Level | | |
| Digester Discharge Liquid Level Variance | | |
| Digester Temperature | | |
| Digester Temperature Variance | | |
| Digester Discharge Valve Opening Maximum | | |
| Digester Discharge Valve Opening Minimum | | |
| Digester Sand Filter Differential Pressure to Maintain | | |
| Digester Discharge Valve Opening % in Manual Mode | | |
| Digester Discharge Delay Time Prior to Opening Discharge Valve | | |
| Digester Feed Rate | | |
| Digester Feed Interval between Feeds in Batch Mode | | |
| Digester Gas Pressure to Open Gas Valve | | |
| Digester Gas Pressure to Close Gas Valve | | |
| Fluidization Time Between Fluidizations | | |
| Fluidization Sand Filter Differential Pressure to Trigger Fluidization | | |
| Fluidization Maximum Time to Complete One Revolution of Sand Blade | | |
| Fluidization Number of Failed Normal Fluidizes to Trigger a Deep Clean | | |
| Fluidization Sand Filter Differential Pressure after a Fluidize to Trigger a Deep Clean | | |
| Separator Tank Discharge Pump On Time | | |
| Separator Tank Discharge Pump Off Time | | |
| Chemical Nutrient Pump On Interval Time | | |
| Chemical Sulfur Pump On Interval Time | | |
| Chemical Anti-Foam Pump On Interval Time | | |
| Chemical Metals Pump On Interval Time | | |
| Chemical Nutrient Pump Cycle On Time | | |
| Chemical Nutrient Pump Cycle Off Time | | |
| Chemical Sulfur Pump Cycle On Time | | |
| Chemical Sulfur Pump Cycle Off Time | | |
| Chemical Anti-Foam Pump Cycle On Time | | |
| Chemical Anti-Foam Pump Cycle Off Time | | |
| Chemical Metals Pump Cycle On Time | | |
| Chemical Metals Pump Cycle Off Time | | |

Equalization (EQ) System

Raw untreated wastewater is pumped from a storage vessel outside of the anaerobic digestion treatment system via the EQ tank feed pump into the EQ tank.

EQ Tank Feed Pump and Valve Control The EQ Tank Feed Pump and EQ Tank Feed Pump Valve turn on at the EQ Tank Feed Pump ON Liquid Level and turn off at the EQ Tank Feed Pump OFF Liquid Level based on the liquid level measured by a pressure transducer in the EQ Tank.

EQ Tank Chemical Addition Pump Controls The chemical (base) addition to the EQ Tank is based on EQ Tank pH, EQ Tank pH Variation and the measurement from the pH sensor in the EQ Tank. The pump turns on when the measured pH in the EQ Tank is less than EQ Tank pH-EQ Tank pH Variation and turns off when the pH is greater than EQ Tank pH.

EQ Tank Mixer Speed Control The EQ Tank Mixer speed is proportionally controlled based on the liquid level in the EQ Tank. The mixer speed varies between EQ Tank Mixer VFD Maximum Speed and EQ Tank Mixer VFD Minimum Speed proportionally as the liquid level varies between EQ Tank Mixer VFD Maximum Speed Liquid Level and EQ Tank Mixer VFD Minimum Speed Liquid Level.

EQ Tank Feed Pump VFD Fault alarm The EQ Tank Feed Pump VFD sends an EQ Tank Feed Pump VFD Fault alarm if a fault occurs in the VFD. The alarm will alert the operator of the fault and shut off the VFD output to the pump.

EQ Tank Mixer VFD Fault alarm The EQ Tank Mixer VFD sends an EQ Tank Mixer VFD Fault alarm if a fault occurs in the VFD. The alarm will shut off the VFD until the fault is manually corrected. The alarm will alert the operator of the fault and shut off the VFD output to the mixer.

EQ Tank Liquid Temperature alarms The EQ Tank has a temperature transducer that measures water temperature in the EQ Tank. There are EQ Tank High Temperature and EQ Tank Low Temperature alarms if the temperature is out of range. The EQ Tank has a tank heater that is not controlled by the software. Both alarms will alert the operator.

EQ Tank Liquid Level alarms The EQ Tank has two liquid level switches. There are EQ Tank High-High Liquid Level and EQ Tank Low-Low Liquid Level alarms if the liquid level is out of range. The EQ Tank High-High Liquid Level alarm will alert the operator and shut off the EQ Tank Feed Pump. The EQ Tank Low-Low Liquid Level alarm will alert the operator and shut off the EQ Tank Mixer and Digester Feed Pump.

EQ Tank Feed Pump Current alarms The EQ Tank Feed Pump VFD outputs the EQ Tank Feed Pump current (amps) to the PLC. There are EQ Tank Feed Pump High Current and EQ Tank Feed Pump Low Current alarms if the current is out of range. Both alarms will alert the operator and shut off the VFD output to the pump.

EQ Tank Mixer Current alarms The EQ Tank Mixer VFD outputs the EQ Tank Mixer current (amps) to the PLC. There are EQ Tank Mixer High Current and EQ Tank Mixer Low Current alarms if the current is out of range. Both alarms will alert the operator and shut off the VFD output to the mixer.

EQ Tank pH alarms The EQ Tank has a pH sensor used to measure pH in the tank. There are EQ Tank High pH and EQ Tank Low pH alarms if the pH is out of range. The EQ Tank High pH alarm will alert the operator and shut off the EQ Tank Chemical Addition Pump and the Digester Feed Pump. The EQ Tank Low pH alarm will alert the operator and shut off the Digester Feed Pump.

Digester Feed (DF) System

Raw wastewater is pumped from the EQ tank to the anaerobic digester where it is treated and discharged.

Digester Feed Pump and Valve Continuous Control The digester feed pump can run in either of two modes, continuous mode or batch mode. In continuous mode, the Digester Feed Pump VFD operates the pump continuously, varying the speed of the pump to maintain a specified flow rate. The specified flow rate is determined by calculating the instantaneous GPM of the pump required to achieve the Digester Feed Pump Daily Gallons. The VFD speed is allowed to vary between Digester Feed Pump VFD Maximum Speed and Digester Feed Pump VFD Minimum Speed If the VFD is required to operate above Digester Feed Pump VFD Maximum Speed, the system alerts the operator that the Digester Feed Pump Daily Gallons must be decreased or the Digester Feed Pump VFD Maximum Speed must be increased. If the VFD is required to operate below the minimum speed, the VFD runs the pump at Digester Feed Pump VFD Minimum Speed cycling the pump on and off as if it were in batch mode.

Digester Feed Pump and Valve Batch Control In batch mode, the VFD operates the pump at Digester Feed Pump VFD Speed. The pump cycles on at Digester Feed Interval between Feeds in Batch Mode intervals. The pump cycles off if either the software calculated required number of gallons per feed interval has successfully fed or the Digester Feed Interval between Feeds in Batch Mode period has elapsed. The Digester Feed Pump will operate if the liquid level in the digester is below Digester Liquid Level. There are two pressure transducers, one being redundant, on the digester to measure the liquid level. The primary pressure transducer is used to determine operation of the Digester Feed Pump.

Digester Feed Pump Flow Totalization

Liquid flow from the Digester Feed Pump passes through a liquid flow meter prior to entering the digester. There is a pulsed output from the flow meter to the PLC. The flow meter outputs one pulse per gallon liquid through flow meter. These pulses are totalized in the PLC and displayed as total gallons pumped through the flow meter by the Digester Feed Pump.

Digester Liquid Level alarms The Digester has two liquid level switches. There are Digester High-High Liquid Level and Digester Low-Low Liquid Level alarms if the liquid level is out of range. The Digester High-High Liquid Level alarm will alert the operator and stop the Digester Feed Pump. The Digester Low-Low Liquid Level alarm will alert the operator and shut off the Digester Discharge Valve.

Digester Foam Level Alarm

The Digester has one liquid level switch used for high-level foam detection. There is a Digester High Foam Level alarm if the foam level is over range. The Digester High Foam Level alarm will alert the operator and shut off the Digester Feed Pump.

Digester Feed Pump Current alarms The Digester Feed Pump VFD outputs the Digester Feed Pump current (amps) to the PLC. There are EQ Tank Feed Pump High Current and EQ Tank Feed Pump Low Current alarms if the current is out of range. Both alarms will alert the operator and shut off the VFD output to the pump.

Digester Feed Pump VFD Fault alarm The Digester Feed Pump VFD sends a Digester Feed Pump VFD Fault alarm if a fault occurs in the VFD. The alarm will alert the operator and shut off the VFD output to the pump.

Digester Liquid Level Transducer Error alarm The liquid level measurement from the primary pressure transducer and liquid level measurement from the redundant pressure transducer varying by more than Digester Liquid Level Transducer Allowable Difference will cause a Digester Liquid Level Transducer Error alarm. The alarm will alert the operator.

Digester Agitator System

There may be two rotating arms in the anaerobic digester used to maintain the digester sand bed filter as well as aid in the mixing of the digester contents. They are the Sand Fluidization Blade and the Sludge Rake Blade. Both blades are operated hydraulically by pumps in the system (Sand Blade Pump and Rake Blade Pump).

Sludge Rake Blade Control The Sludge Rake Blade is used to "rake" the sludge/biomass layer directly on top of the sand bed filter in the anaerobic digester. This raking effect aids in increasing the effluent discharge flow from the digester. The sludge rake blade pump can run in either of two modes, continuous mode or intermittent mode. In continuous mode, the VFD that controls the rake blade pump runs continuously, varying the speed of the Rake Blade Pump between Rake Blade Pump VFD Maximum Speed (Rake Mode) and Rake Blade Pump VFD Minimum Speed (Rake Mode) to control the rotational speed of the rake blade. In intermittent mode, the VFD turns on and off for Rake Blade Pump Intermittent Mode On Time and Rake Blade Pump Intermittent Mode Off Time periods while still varying the speed of the rake blade pump to control the rotational speed of the rake blade. The rake blade may be mechanically (e.g., gear, planetary gear, shaft, belt, magnetic drive, piston or any other mechanically transmitted power drive) or pneumatically (hydraulically, fluid pressure or air pressure) driven for purposes of this technology. Magnetic switches that actuate as the blade rotates determine the rotational speed of the Rake Blade. The time between switch actuations (clicks) is measured by the PLC. The Rake Blade RPM is calculated from the time between clicks. The Rake Blade VFD output is adjusted up or down based on the current RPM compared to the Rake Blade RPM. If the time between clicks is too long (i.e. the blade is moving too slow) the VFD output is increased incrementally speeding up the Rake Blade, if the time between clicks is too short (i.e. the blade is moving too fast) the VFD output is decreased incrementally slowing down the Rake Blade.

Normal Fluidization Control The sand fluidization blade is used to "fluidize" the sand bed filter in the anaerobic digester to prevent the sand bed from getting "packed" and restricting effluent flow. A fluidization cycle is started in either of two ways. If the Fluidization Time between Fluidizes period elapses without a fluidize cycle, one will begin. A fluidize cycle will also begin based on the differential pressure measured across the sand filer bed. When the digester is discharging and the differential pressure across the sand filter bed becomes greater than Fluidization Sand Filter Differential Pressure to Trigger Fluidize, the discharge will stop and a fluidize cycle will begin.

The Rake Blade Pump is used to hydraulically propel the Fluidization Blade through the sand filter during a fluidize cycle. The Sand Fluidization Pump is used to "fluidize" the sand in front of the rotating blade, allowing it to be propelled through the sand bed. The Rake Blade Pump VFD initially starts at Rake Blade Pump Initial VFD Speed (Propulsion Mode) and varies the speed between the Rake Blade Pump Maximum VFD Speed (Propulsion Mode) and Rake Blade Pump Minimum VFD Speed (Propulsion Mode) based on the rotational speed of the sand blade. The Sand Fluidization Blade VFD initially starts at Sand Fluidization Pump Initial VFD Speed and is capable of varying the speed between the Sand Fluidization Pump Maximum VFD Speed and Sand Fluidization Pump Minimum VFD Speed Magnetic switches that are actuated as the blade rotates determine the rotational speed of the Fluidization Blade. The time between switch actuations (clicks) is measured by the PLC. The Fluidization Blade RPM is calculated from the time between clicks. The Sand Blade Pump VFD speed is adjusted up or down based on the calculated RPM compared to the Fluidization Blade (Normal Fluidize) RPM. If the time between clicks is too long (i.e. the Fluidization Blade is moving too slow) the VFD output is increased incrementally speeding up the Fluidization Blade, if the time between clicks is too short (i.e. the Fluidization Blade is moving too fast) the VFD output is decreased incrementally slowing down the Fluidization Blade. A successful fluidize cycle is recorded when a set number of clicks are recorded during a fluidize cycle. An unsuccessful fluidize cycle is recorded when Normal Fluidization—Time to Complete elapses before a successful fluidize. If the number of unsuccessful fluidizes exceeds Deep Clean Fluidization—Number of Failed Normal Fluidizes to Start Deep Clean a Deep Clean Fluidize cycle will start.

Deep Clean Fluidization Control A Deep Clean Fluidize is a fluidize cycle where the Rake Blade Pump (in propulsion mode) runs at a slower speed than in the Normal Fluidize Cycle to more thoroughly fluidize the sand bed compared to a Normal Fluidize.

A Deep Clean Fluidize is initiated when the time to perform a successful normal fluidize is less than Normal Fluidization—Time to Complete, a successful normal fluidize has not occurred during Deep Clean Fluidization—Number of Failed Normal Fluidizes to Start Deep Clean or after a successful Normal Fluidize, the differential pressure across the Sand Filter Bed exceeds Fluidization Sand Filter Differential Pressure after a Fluidize to Trigger a Deep Clean. The Sand Blade Pump VFD speed is controlled the same way it is in a Normal Fluidize. The Sand Blade Pump VFD speed is adjusted up or down based on the calculated RPM compared to the Fluidization Blade (Deep Clean) RPM.

Sludge Rake Blade Pump Current alarms The Sludge Rake Blade Pump VFD outputs the Sludge Rake Blade Pump current (amps) to the PLC. There are Sludge Rake Blade Pump High Current and Sludge Rake Blade Pump Low Current alarms if the current is out of range. Both alarms will alert the operator and shut off the VFD output to the pump.

Sand Fluidization Blade Pump Current alarms The Sand Fluidization Blade Pump VFD outputs the Sand Fluidization Blade Pump current (amps) to the PLC. There are Sand Fluidization Blade Pump High Current and Sand Fluidization Blade Pump Low Current alarms if the current is out of range. Both alarms will alert the operator and shut off the VFD output to the pump.

Sludge Rake Blade Pump Pressure alarms The Sludge Rake Blade Pump has a pressure transducer on its effluent side. There are Sludge Rake Blade Pump High Pressure and Sludge Rake Blade Pump Low Pressure alarms if the pressure is out of range. Both alarms will alert the operator and shut off the VFD output to the pump.

Sand Fluidization Blade Pump Pressure alarms The Sand Fluidization Blade Pump has a pressure transducer on its effluent side. There are Sand Fluidization Blade Pump High Pressure and Sand Fluidization Blade Pump Low Pressure alarms if the pressure is out of range. Both alarms will alert the operator and shut off the VFD output to the pump.

Sludge Rake Blade Pump VFD Fault alarm The Sludge Rake Blade Pump VFD sends a Sludge Rake Blade Pump VFD Fault alarm if a fault occurs in the VFD. The alarm will alert the operator and shut off the VFD output to the pump.

Sand Fluidization Blade Pump VFD Fault alarm The Sand Fluidization Blade Pump VFD sends a Sand Fluidization Blade Pump VFD Fault alarm if a fault occurs in the VFD. The alarm will alert the operator and shut off the VFD output to the pump.

Digester Discharge Control The anaerobic digester discharges water in order to maintain a liquid level in the tank.

Digester Discharge Valve Control The anaerobic digester has an actuated valve on the discharge that is adjusted based on the differential pressure across the Sand Filter Bed when the digester is discharging. The discharge valve's percentage open is adjusted up and down between Digester Discharge Valve Opening Maximum and Digester Discharge Valve Opening Minimum to maintain Digester Sand Filter Differential Pressure to Maintain. The digester will begin to discharge water when the liquid level in the digester is greater than Digester Liquid Level. When the digester is discharging and the Sand Filter Bed is becoming "packed", the differential pressure across the Sand Filter Bed will become greater than Fluidization Sand Filter Differential Pressure to Trigger Fluidize and a Normal Fluidize cycle will start. When the fluidize cycle is finished, if the liquid level in the digester is still above Digester Liquid Level minus Digester Liquid Level Variance the digester discharge valve will begin the discharge-fluidize cycle again until the liquid level is below Digester Liquid Level minus Digester Liquid Level Variance.

Digester Effluent Flow Totalization Discharge liquid flow from the digester passes through a liquid flow meter prior to entering the Gas Separation Tank. There is a pulsed output from the flow meter to the PLC. The flow meter outputs one pulse per gallon liquid through flow meter. These pulses are totalized in the PLC and displayed as total gallons discharged from the digester.

Gas Separation Tank Liquid Level alarm The Gas Separation Tank has one liquid level switch used for high liquid level detection. There is a Gas Separation Tank Liquid Level alarm if the liquid level is over range. The Gas Separation Tank Liquid Level alarm will alert the operator and close the digester valve.

Foam Lockout Control

Gas handling is required as gas generated inside the digester, passes to the gas separation tank. This gas is combined with the separated gas from the discharge water. A sample of this combined gas is pumped through a gas analyzer. The remaining gas passes through a flow meter and discharged to a flare or other gas processing equipment.

Gas Analyzer Drain Control The gas that passes to the gas analyzer contains moisture. This moisture is collected and the Gas analyzer drain pump is activated to drain the condensate collector.

Gas Pressure Alarm

A pressure transducer continuously monitors digester headspace pressure. When the gas pressure reaches Digester Gas Pressure to Open Gas Valve, a solenoid valve opens and gas is released through the flow meter and subsequently to the flare. This valve stays open until the pressure measured reaches Digester Gas Pressure to Close Gas Valve. To prevent any liquid from entering the gas process piping a solenoid valve is located at the beginning of the gas piping. If a Digester High Foam Level or a Gas Separation Tank Liquid Level alarm is detected, this valve will close until the alarm is cleared.

The Digester Gas Discharge has a pressure transducer on its effluent side. There is a Digester Gas Discharge High Pressure alarm if the pressure is out of range. The alarm will alert the operator and cause a Foam Lockout Alarm.

Digester Temperature Control

A digester heater maintains a constant temperature in the digester.

Digester Liquid Temperature Control The digester heater is turned on and off based on Digester Temperature and Digester Temperature Variance. The digester heater turns on when the temperature is less than Digester Temperature—Digester Temperature Variance and turns off when the temperature is above Digester Temperature.

Digester Liquid Temperature alarms There are Digester Temperature High and Digester Temperature Low alarms if the digester temperature is out of range. Both alarms will alert the operator.

Chemical Addition System

There are four metering pumps used to supply supplemental chemicals to the digester. They are the Base Pump, Nutrients Pump, Sulfur Pump, and Metals Pump.

Digester Chemical Recirculation Pump Control The Digester Chemical Recirculation Pump is used to provide recirculation of digester contents and allow for chemical addition to the digester. No alarms cause the Recirculation Pump to shut off.

Digester Liquid pH alarms The Digester has two pH sensor used to measure pH in the tank. There are Digester High pH and Digester Low pH alarms if the pH is out of range. The Digester High pH alarm will alert the operator and shut off the Base Addition Pump. The Digester Low pH alarm will alert the operator.

Digester Chemical Recirculation Pump Liquid Pressure Alarms

The Chemical Recirculation Pump has a pressure transducer on its effluent side. There are Chemical Recirculation Pump High Pressure and Chemical Recirculation Pump Low Pressure alarms if the pressure is out of range. Both alarms will alert the operator. Digester Chemical Recirculation Pump VFD Fault alarm The Chemical Recirculation Pump VFD sends a Chemical Recirculation Pump VFD Fault alarm if a fault occurs in the VFD. The alarm will alert the operator and shut off the VFD output to the pump. Base Pump Two chemical feed pumps are used to add base to the system. One of the pumps adds base to EQ tank and the other pump adds base to the digester. Both base pumps operate the same way. The EQ Tank Base pump turns on when the measured pH in the EQ Tank is less than EQ Tank pH—EQ Tank pH Variation and turns off when the pH is greater than EQ Tank pH The Digester Base pump turns on when the measured pH in the Digester is less than Digester pH—Digester pH Variation and turns off when the pH is greater than Digester pH. Nutrient Pump—The Nutrient Pump is a metering pump that adds nutrients to the Digester. The Nutrient Pump has three adjustable settings. They are Nutrient Pump Capacity (GPD), Nutrient Pump Flow (GPD) and Nutrient Pump Pumping Interval. Nutrient Pump Flow is divided by Nutrient Pump Capacity to calculate the amount of time during the day the pump has to run. The required daily run time of the pump is divided into intervals based on Nutrient Pump Pumping Interval and the pump on and off times per interval are calculated. Sulfur Pump—The Sulfur Pump is a metering pump that adds sulfur to the Digester. The Sulfur Pump has three adjustable settings. They are Sulfur Pump Capacity (GPD), Sulfur Pump Flow (GPD) and Sulfur Pump Pumping Interval. Sulfur Pump Flow is divided by Sulfur Pump Capacity to calculate the amount of time during the day the pump has to run. The required time is divided into equal intervals based on Sulfur Pump Pumping Interval and the pump on and off times are calculated. Metals Pump—The Metals Pump is a metering pump that adds metals to the Digester. The Metals Pump has three adjustable settings. They are Metals Pump Capacity (GPD), Metals Pump Flow (GPD) and Metals Pump Pumping Interval. Metals Pump Flow is divided by Metals Pump Capacity to calculate the amount of time during the day the pump has to run. The required time is divided into equal intervals based on Metals Pump Pumping Interval and the pump on and off times are calculated. Anti-Foam Pump The Anti-Foam Pump is a metering pump that adds sulfur to the Digester. The Anti-Foam Pump has three adjustable settings. They are Anti-Foam Pump Capacity (GPD), Anti-Foam Pump Flow (GPD) and Anti-Foam Pump Pumping Interval. Anti-Foam Pump Flow is divided by Anti-Foam Pump Capacity to calculate the amount of time during the day the pump has to run. The required time is divided into equal intervals based on Anti-Foam Pump Pumping Interval and the pump on and off times are calculated.

Other On-Line Instruments

System Air Pressure alarm The System Air Pressure has a pressure switch associated with it. There is a System Air Pressure Low alarm if the pressure is out of range. The alarm will alert the operator.

Additional considerations and controls applied in the Digester System may include one or more of the following Additional parameters involving the digester:
1. Intermediate degradation component detection and control
   a. Intermediate degradation components can be monitored and information sent to the PLC. System variables such as pH, feed rate and alkalinity can be adjusted to maintain the process.
2. Contaminant alarm
   a. The process can be monitored for the presence of contaminants (such as quaternary ammonium) with information being sent to the PLC to cause alarm conditions.
3. Solids concentration monitoring and control
   a. Detection of the solids concentration in the digester is sent to the PLC to allow the system to adjust system parameters such as feed rate to maintain the process.
4. BOD and COD monitoring and control
   a. Near real-time monitoring of COD and/or BOD allowing the PLC to adjust system parameters such as feed rate and pH to maintain the process.
5. Surface tension/foam detection monitoring and alarm
   a. Surface tension is monitored sending information to the PLC to cause an alarm condition if the surface tension is outside of acceptable user selectable parameters.
6. Fats, Oils, and Grease (FOG) monitoring and alarm
   a. FOG is monitored sending information to the PLC allowing system parameters such as feed rate and feed type to be adjusted to maintain the process. An alarm condition is triggered when FOG levels are outside of user selectable parameters.
7. Dissolved gas monitoring and alarm
   a. Dissolved gas is monitored sending information to the PLC allowing system parameters such as feed rate and feed type to be adjusted to maintain the process. An alarm condition is triggered when dissolved gas levels are outside of user selectable parameters.
8. Volatile acids monitoring and alarm
   a. Volatile acids concentration is monitored sending information to the PLC allowing system parameters such as feed rate and feed type to be adjusted to maintain the process. An alarm condition is triggered when volatile acids concentration levels are outside of user selectable parameters.
9. Detection and control of specific bacteria concentration/activity
   a. The activity of specific bacteria may be monitored and other system parameters such as feed rate may be adjusted to maintain desired activity level and/or concentration Titration A NewBio® systems designed titrator is incorporated in the system for checking critical data. This titrator consists of instrumentation and control valves that are controlled via the PLC. The titrator consists of independent, dedicated solenoid valves that are connected to the following input sample points:
1. 2 foot Digester port
2. 4 foot Digester port
3. 6 foot Digester port
4. 8 foot Digester Port
5. Influent
6. Effluent
7. Ad-Hoc The titrator also may have the following:
1. DI water (used for rinses)
2. CDA (Clean Dry Air) (Used for Rinses)
3. Drain solenoid valve
4. Feed pump
5. Sample bottle
6. Sample stirrer
7. pH probe
8. Metering pump (for pumping acid)
9. Purge Solenoid valve
10. Drain Solenoid Valve The titrator is used to run two pre-programmed routines. The first routine only checks for initial pH. The second routine tests for the following: pH, Alkalinity, Volatile Acids. The pre-programmed routines proceed in a stepwise fashion through the following steps:
1. Sample Preparation
2. Initial pH
3. Initial Volatile Acids Step
4. Alkalinity Determination
5. Final Volatile Acids Step
6. Equipment Cleaning.

For each test, samples may be automatically taken from the above listed sample points at user selectable sampling intervals (intervals for each sampling point will be different).

The Acid Metering pump may operate by dispensing a known volume of Acid each time it receives a discrete signal to initiate pumping. The PLC shall operate the pump by making an 110V contact closure signal. The pump shall then dispense a known quantity of acid (typically 20 micro liters) into the titration vessel. There shall be a time delay between discrete signals, settable by the HMI (typically 3 seconds), to allow time for the mixer to disperse the acid, and obtain a valid pH reading.

The mixer should be always on.

Sample Preparation

At the beginning of each cycle, clean water is in the Titration Vessel (as the last step in the Equipment cleaning process). In addition, prior to collecting the sample to be analyzed, sample material shall be purged directly to drain, to assure that a valid sample is being tested. Since the physical distance to the sample port is different for each port, the quantity of sample to be purged is different for each selected sample. This shall be controlled by the quantity of time that the purge valve is open, and shall be individually changeable via the HMI. Sample preparation shall proceed as follows: 1. Open drain solenoid valve to empty titration vessel, for a time adjustable via the HMI. 2. Close drain valve. 3. Open Purge valve, and selected sample port valve, for a quantity of time settable via the HMI. The specific sample port valve (2 foot, 4 foot, 6 foot, 8 foot, influent, effluent, or Ad-Hoc valve) shall be selected via the HMI. At the same time turn on feed pump (p-10). 4. At the end of the purge cycle, close the sample port valve, turn off the feed pump and close the purge valve. 5. Open the CDA Valve to push the sample into the titration vessel. The quantity of time that the CDA valve will be open shall be settable via the HMI (typically 20 seconds). 6. Close the CDA Valve. 7. Sample preparation is complete.

pH

Collecting an accurate initial pH is generally the first step in all of the pre-programmed routines. To test for pH, the titrator shall do the following: 1. Wait a predetermined quantity of time to allow sample stabilization prior to recording the initial pH (typically 20 seconds). This time delay shall be settable via the HMI. 2. Take pH reading. When the pH varies by less than 0.02 pH units in a 5-second period, store the data in a form usable to the HMI interface. 3. If the pH is the only item requested by the HMI, proceed to the Equipment Cleaning procedure.

Alkalinity and Volatile Acids
1. Collect an initial pH (per above procedure).
2. Add in acid, using discrete pulses to the Acid metering pump (as described above), and record the number of pulses required to reduce the initial pH to pH 5.00.
3. Continue to add acid, using discrete pulses to the Acid metering pump (as described above), and record the number of pulses required to reduce the initial pH to pH 4.30.
4. Continue to add acid, using discrete pulses to the Acid metering pump (as described above), and record the number of pulses required to reduce the initial pH to pH 4.00.
5. If the pH of 4.00 cannot be reached within a maximum number of acid additions settable by the operator (typically 200 cycles), end the procedure and set an alarm for the HMI.
6. Calculation of the Alkalinity and Volatile Acids shall be performed in the HMI and shall use the recorded values.

Equipment Cleaning
1. After the sample analysis is complete, open the Titrator vessel drain valve, the DI valve and the purge valve, for a time settable by the HMI (typically 20 seconds). 2. Close the valves. 3. Open the DI valve for a time settable by the HMI to put excess DI water into the titrator vessel. 4. Close the DI valve. 5. Open the CDA valve for a time settable by the HMI to push DI water into the vessel. 6. Open the drain valve to drain the titrator vessel. 7. Close the titrator drain valve. 8. Open the purge valve and the DI water valve, for a time settable by the HMI. 9. Close the valves. 10. Repeat steps 3-8 for a number of repetitions settable by the HMI (typically 2). 11. For the final rinse cycle repeat steps 3-5. 12. Equipment cleaning step is now complete.

Software Content

The software (where used) can be provided in any operative language or code useful for operation of the system. Examples of actual software used in a typical operation of a sense and response system are provided below and in Appendices of the ladder step details of the procedures filed with this application and incorporated herein by reference for the:

Digester Discharge

XIO I:7.0/11 NXB XIC T4:29/DN BND XIO B3:0/1 BST TON T4:29 1.0 5 0 NXB XIC T4:29/DN OTE N9:17/11 BND

1. XIC I:6.0/11 XIO N9:21/2 XIO N9:21/3 XIC I:7.0/10 XIC I:7.0/11 XIC I:7.0/9 XIC N9:21/11 BST XIC T4:73/DN OTE B3:1/0 NXB OTE N9:21/14 BND

2. BST CPT F8:7 N9:2−((N9:5−5000.0)*0.12042) NXB MOV F8:7 N9:112 BND

3. BST SUB N10:66 N10:13 N9:109 NXB BST GRT N9:112 N10:66 NXB XIC N9:21/11 BND GRT N9:112 N9:109 OTE N9:21/11 BND

4. BST MOV N10:100 T4:73.PRE NXB XIC N9:21/14 TON T4:73 1.0 60 0 BND

5. BST SUB N9:2 N9:64 N9:47 NXB LES N9:47 0 MOV 0 N9:47 NXB GRT N9:47 N10:33 OTE B3:1/1 NXB LES N9:47 N10:33 OTE B3:1/2 NXB GRT N9:47 N10:44 TON T4:47 1.0 5 0 BND

6. XIC B3:1/0 BST XIC T4:12/DN BST XIC B3:1/1 SUB N9:81 50 N9:81 NXB XIC B3:1/2 ADD N9:81 50 N9:81 BND NXB LES N9:81 N10:45 MOV N10:45 N9:81 NXB GRT N9:81 N10:46 MOV N10:46 N9:81 NXB LES N10:46 N10:45 MOV 10000 N10:46 BND

7. XIC I:6.0/10 XIO N9:21/2 XIO N9:21/3 XIC I:7.0/9 MOV N10:71 N9:81

8. BST XIO I:6.0/11 XIO I:6.0/10 NXB XIC N9:21/2 NXB XIC N9:21/3 NXB XIC I:6.0/11 XIO B3:1/0 BND MOV 0 N9:81

9. GRT N9:81 0 OTE O:1.0/13

10. BST XIC I:6.0/11 BST XIC B3:1/0 OTE N9:94/1 NXB XIO B3:1/0 OTE N9:94/2 BND NXB XIO I:6.0/11 XIO I:6.0/10 OTE N9:94/3 NXB XIC I:6.0/10 OTE N9:94/4 BND

11. XIC N9:17/11 OTE N9:94/5

12. BST BST BST XIC I:8.0/2 NXB XIC O:3.0/3 BND XIC I:7.0/14 XIC I:6.0/13 XIC I:7.0/11 NXB XIC I:6.0/12 BND BST OTE O:3.0/3 NXB OTE O:1.0/14 BND NXB XIC O:3.0/3 MOV N10:123 N9:161 NXB XIO O:3.0/3 MOV 0 N9:161 BND

13. BST XIC I:6.0/13 BST XIC O:3.0/3 OTE N9:94/6 NXB XIO O:3.0/3 OTE N9:94/7 BND NXB XIO I:6.0/13 XIO I:6.0/12 OTE N9:94/8 NXB XIC I:6.0/12 OTE N9:94/9 BND

14. XIC B3:0/0 OTE N9:94/10

15. BST BST BST XIC I:8.0/0 NXB XIC O:2.0/13 BND XIC I:8.0/1 XIC I:6.0/15 XIC I:7.0/11 NXB XIC I:6.0/14 BND BST OTE O:2.0/13 NXB OTE O:1.0/15 BND NXB XIC O:2.0/13 MOV N10:122 N9:160 NXB XIO O:2.0/13 MOV 0 N9:160 BND

16. BST XIC I:6.0/15 BST XIC O:2.0/13 OTE N9:95/0 NXB XIO O:2.0/13 OTE N9:95/1 BND NXB XIO I:6.0/15 XIO I:6.0/14 OTE N9:95/2 NXB XIC I:6.0/14 OTE N9:95/3 BND

17. XIC B3:0/0 OTE N9:95/4

18. BST XIC B3:2/3 OSR B3:2/4 ADD F8:6 1.0 F8:6 NXB XIO I:8.0/13 TON T4:78 1.0 0 0 NXB BST XIC I:8.0/13 NXB XIC B3:2/3 BND XIO T4:78/DN OTE B3:2/3 BND

19. BST BST XIC I:8.0/8 NXB XIC I:8.0/9 XIO N9:21/12 LEQ N9:113 N10:117 BND BST OTE O:3.0/14 NXB OTE O:2.0/0 BND NXB BST XIO I:8.0/9 NXB XIC N9:21/12 NXB LEQ N9:113 0 BND ADD N10:117 N10:118 N9:113 NXB XIC I:8.0/9 XIO N9:21/12 XIC T4:14/DN SUB N9:113 1 N9:113 NXB XIC O:3.0/14 MOV N10:124 N9:72 NXB XIO O:3.0/14 MOV 0 N9:72 BND

20. BST XIC I:8.0/9 BST XIC O:3.0/14 OTE N9:94/11 NXB XIO 0:3.0/14 OTE N9:94/12 BND NXB XIO I:8.0/9 XIO I:8.0/8 OTE N9:94/13 NXB XIC I:8.0/8 OTE N9:94/14 BND

0. BST

Titration Tester/Sensor

0. GRT N10:60 0 BST BST MOV N9:24 N9:86 NXB MOV N10:60 N9:87 NXB MOV 0 N9:34 NXB MOV 0 N9:35 NXB MOV 0 N9:36 NXB MOV 0 N9:37 NXB MOV 0 N9:88 BND NXB LES N10:60 20 EQU N9:32 0 MOV 1 N9:32 NXB EQU N10:60 20 MOV 0 N9:32 NXB EQU N10:60 21 MOV 21 N9:32 NXB MOV 0 N10:60 BND

1. BST MOV N10:84 T4:53.PRE NXB EQU N9:32 1 BST OTE N9:33/0 NXB TON T4:53 1.0 90 0 NXB XIC T4:53/DN MOV 2 N9:32 BND BND

2. BST MOV N10:93 T4:54.PRE NXB EQU N9:32 2 BST OTE N9:33/1 NXB TON T4:54 1.0 40 0 NXB XIC T4:54/DN MOV 3 N9:32 BND BND

3. BST MOV N10:85 T4:55.PRE NXB EQU N9:32 3 BST OTE N9:33/2 NXB TON T4:55 1.0 7 0 NXB XIC T4:55/DN MOV 4 N9:32 BND BND

4. BST MOV N10:86 T4:56.PRE NXB EQU N9:32 4 BST OTE N9:33/3 NXB TON T4:56 1.0 10 0 NXB CPT F8:3 ((((N9:100+N9:101)+N9:102)+N9:103)+N9:104)5.0 NXB MOV F8:3 N9:105 NXB SUB N9:105 N9:53 N9:106 NXB ABS N9:106 N9:106 NXB XIC T4:56/DN LEQ N9:106 N10:94 OTE B3:1/12 NXB XIC T4:12/DN BST MOV N9:103 N9:104 NXB MOV N9:102 N9:103 NXB MOV N9:101 N9:102 NXB MOV N9:100 N9:101 NXB MOV N9:53 N9:100 BND NXB XIC T4:56/DN XIC B3:1/12 BST TON T4:68 1.0 5 0 NXB XIC T4:68/DN BST MOV N9:53 N9:34 NXB GRT N9:87 10 MOV 10 N9:32 NXB LES N9:87 10 MOV 21 N9:32 BND BND BND BND

5. EQU N9:32 10 BST OTE N9:33/4 NXB LEQ N9:53 N10:99 BST MOV N9:88 N9:108 NXB MOV 11 N9:32 BND BND

6. EQU N9:32 11 BST OTE N9:33/4 NXB LEQ N9:53 N10:95 BST MOV N9:88 N9:35 NXB MOV 12 N9:32 BND BND

7. EQU N9:32 12 BST OTE N9:33/5 NXB LEQ N9:53 N10:96 BST MOV N9:88 N9:36 NXB MOV 13 N9:32 BND BND

8. EQU N9:32 13 BST OTE N9:33/6 NXB LEQ N9:53 N10:97 BST MOV N9:88 N9:37 NXB MOV 21 N9:32 BND BND

9. BST MOV N10:88 T4:57.PRE NXB EQU N9:32 21 BST OTE N9:33/7 NXB MOV N10:92 N9:89 NXB TON T4:57 1.0 90 0 NXB XIC T4:57/DN MOV 22 N9:32 BND BND

10. EQU N9:32 22 BST OTE N9:33/8 NXB TON T4:63 0.01 50 0 NXB XIC T4:63/DN MOV 23 N9:32 BND

11. BST MOV N10:89 T4:58.PRE NXB EQU N9:32 23 BST OTE N9:33/9 NXB TON T4:58 1.0 7 0 NXB XIC T4:58/DN MOV 24 N9:32 BND BND

12. EQU N9:32 24 BST OTE N9:33/10 NXB TON T4:67 0.01 10 0 NXB XIC T4:67/DN MOV 25 N9:32 BND

13. BST MOV N10:90 T4:59.PRE NXB EQU N9:32 25 BST OTE N9:33/11 NXB TON T4:59 1.0 5 0 NXB XIC T4:59/DN BST GRT N9:89 0 MOV 26 N9:32 NXB EQU N9:89 0 MOV 0 N9:32 BND BND BND

14. BST MOV N10:98 T4:64.PRE NXB EQU N9:32 26 BST OTE N9:33/12 NXB TON T4:64 1.0 90 0 NXB XIC T4:64/DN MOV 27 N9:32 BND BND

15. EQU N9:32 27 BST OTE N9:33/13 NXB TON T4:65 0.01 50 0 NXB XIC T4:65/DN MOV 28 N9:32 BND

16. BST MOV N10:91 T4:60.PRE NXB EQU N9:32 28 BST OTE N9:33/14 NXB TON T4:60 1.0 7 0 NXB XIC T4:60/DN MOV 29 N9:32 BND BND

17. EQU N9:32 29 BST OTE N9:33/15 NXB TON T4:66 0.01 50 0 NXB XIC T4:66/DN BST GRT N9:89 0 SUB N9:89 1 N9:89 NXB MOV 23 N9:32 BND BND

18. BST XIC N9:33/1 NXB XIC N9:33/9 NXB XIC N9:33/14 BND OTE O:4.0/0

19. XIC N9:33/1 OTE O:4.0/1

20. BST XIC N9:33/2 NXB XIC N9:33/11 NXB XIC N9:33/14 BND OTE O:4.0/2

21. XIC N9:33/9 OTE O:4.0/3

22. XIC N9:33/1 BST EQU N9:87 7 NXB EQU N9:87 17 BND OTE O:4.0/4

23. XIC N9:33/1 BST EQU N9:87 6 NXB EQU N9:87 16 BND OTE O:4.0/5

24. XIC N9:33/BST EQU N9:87 5 NXB EQU N9:87 15 BND OTE O:4.0/6

25. XIC N9:33/1 BST EQU N9:87 4 NXB EQU N9:87 14 BND OTE O:4.0/7

26. XIC N9:33/1 BST EQU N9:87 3 NXB EQU N9:87 13 BND OTE O:4.0/8

27. XIC N9:33/1 BST EQU N9:87 2 NXB EQU N9:87 12 BND OTE O:4.0/9

28. XIC N9:33/1 BST EQU N9:87 1 NXB EQU N9:87 11 BND OTE O:4.0/10

29. BST XIC N9:33/0 NXB XIC N9:33/7 NXB XIC N9:33/12 BND OTE O:4.0/11

30. BST XIC O:4.0/2 NXB XIC O:4.0/3 BND OTE O:4.0/13

31. BST BST XIC N9:33/4 NXB XIC N9:33/5 NXB XIC N9:33/6 BND BST XIO T4:62/DN BST OTE O:3.0/10 NXB OSR B3:1/13 ADD N9:88 1 N9:88 BND NXB XIO T4:61/DN TON T4:62 0.01 50 0 NXB XIC T4:62/DN TON T4:61 1.0 3 0 BND NXB MOV N10:83 T4:61.PRE BND

32. BST BST XIC N9:33/4 NXB XIC N9:33/5 NXB XIC N9:33/6 BND GRT N9:88 N10:87 NXB XIC N9:18/6 BND XIO B3:0/1 BST OTE N9:18/6 NXB OSR B3:1/14 MOV 21 N9:32 BND

Digester Fluidizer

1. XIC B3:0/0 BST BST XIC N9:21/2 NXB XIC N9:21/3 BND GRT N9:65 N10:14 NXB XIC T4:16/DN BND XIO B3:0/1 BST TON T4:16 1.0 5 0 NXB XIC T4:16/DN OTE N9:16/11 BND

2. XIC B3:0/0 BST BST XIC N9:21/2 NXB XIC N9:21/3 BND XIC O:2.0/15 LES N9:65 N10:15 NXB XIC T4:17/DN BND XIO B3:0/1 BST TON T4:17 1.0 5 0 NXB XIC T4:17/DN OTE N9:16/12 BND

3. XIC B3:0/0 BST BST XIC N9:21/2 NXB XIC N9:21/3 BND GRT N9:15 N10:68 NXB XIC T4:18/DN BND XIO B3:0/1 BST TON T4:18 1.0 5 0 NXB XIC T4:18/DN OTE N9:16/13 BND

4. XIC B3:0/0 BST BST XIC N9:21/2 NXB XIC N9:21/3 BND XIC O:2.0/14 LES N9:15 N10:69 NXB XIC T4:19/DN BND XIO B3:0/1 BST TON T4:19 1.0 5 0 NXB XIC T4:19/DN OTE N9:16/14 BND

5. XIC B3:0/0 BST BST XIC N9:21/2 NXB XIC N9:21/3 BND GRT N9:52 N10:20 NXB XIC T4:20/DN BND XIO B3:0/1 BST TON T4:20 1.0 5 0 NXB XIC T4:20/DN OTE N9:17/3 BND

6. XIC B3:0/0 BST BST XIC N9:21/2 NXB XIC N9:21/3 BND LES N9:52 N10:21 NXB XIC T4:21/DN BND XIO B3:0/1 BST TON T4:21 1.0 5 0 NXB XIC T4:21/DN OTE N9:17/4 BND

7. XIC B3:0/0 BST BST XIC N9:21/2 NXB XIC N9:21/3 BND GRT N9:51 N10:22 NXB XIC T4:22/DN BND XIO B3:0/1 BST TON T4:22 1.0 5 0 NXB XIC T4:22/DN OTE N9:17/5 BND

8. XIC B3:0/0 BST BST XIC N9:21/2 NXB XIC N9:21/3 BND LES N9:51 N10:23 NXB XIC T4:23/DN BND XIO B3:0/1 BST TON T4:23 1.0 5 0 NXB XIC T4:23/DN OTE N9:17/6 BND

9. XIC N9:21/2 GRT N9:26 8 BST OTE B3:0/6 NXB MOV N9:44 N9:45 BND

10. XIC N9:21/3 GRT N9:26 N10:36 OTE B3:0/12

11. BST XIC N9:21/2 NXB XIC N9:21/3 BND MOV N10:32 N9:29

12. XIC I:5.0/11 BST XIO N9:21/2 XIO N9:21/3 XIC T4:14/DN GRT N9:29 0 SUB N9:29 1 N9:29 NXB LEQ N9:29 0 OTE N9:21/4 BND

13. BST XIC N9:21/2 NXB XIC N9:21/3 BND BST XIC T4:12/DN LES N9:44 30000 ADD N9:44 1 N9:44 NXB OSR B3:1/11 MOV 0 N9:44 BND

14. BST XIO N9:21/3 XIC N9:21/4 NXB XIO N9:21/3 XIC T4:47/DN NXB XIO N9:21/3 XIC N10:0/0 NXB XIC N9:21/2 BND XIO B3:0/5 XIO B3:0/6 XIC I:5.0/11 XIC I:5.0/13 BST OTE N9:21/2 NXB BST OTU N10:0/0 NXB OSR B3:0/11 MOV N9:24 N9:30 BND BND BST XIO N9:21/2 XIC B3:0/0 LES N9:45 N10:28 NXB XIO N9:21/2 GEQ N9:38 N10:30 NXB XIO N9:21/2 XIC N10:0/1 NXB XIC N9:21/3 BND XIO B3:0/5 XIO B3:0/12 XIC I:5.0/11 XIC I:5.0/13 BST OTE N9:21/3 NXB OTU N10:0/1 NXB MOV N10:28 N9:45 NXB MOV 0 N9:38 BND

15. XIO N9:17/4 XIO N9:17/3 XIO N9:17/6 XIO N9:17/5 XIO N9:16/12 XIO N9:16/14 LES N9:43 N10:29 OTE B3:0/7

16. XIO B3:0/7 BST OTE B3:0/5 NXB XIC N9:21/2 OSR B3:1/9 ADD N9:38 1 N9:38 BND

17. BST XIC N9:21/2 NXB XIC N9:21/3 BND OSR B3:0/8 BST MOV 0 N9:26 NXB MOV 0 N9:27 NXB MOV 0 N9:40 BND

18. XIC I:7.0/6 OSR B3:0/9 OTE B3:1/6

19. XIC I:7.0/13 OSR B3:0/10 OTE B3:1/7

20. XIC B3:1/6 ADD N9:26 1 N9:26

21. XIC B3:1/7 ADD N9:27 1 N9:27

22. XIC I:5.0/10 MOV N10:34 N9:73

23. BST XIC N9:21/3 LES N9:26 2 OSR B3:1/15 MOV N10:35 N9:73 NXB XIC N9:21/2 LES N9:26 2

OSR B3:2/0 MOV N10:110 N9:73 NXB XIC N9:21/2 MOV N10:109 N10:39 NXB XIC N9:21/3 M4V N10:108 N10:39 BND

24. BST XIC N9:21/3 NXB XIC N9:21/2 BND XIC T4:13/DN ADD N9:43 1 N9:43

25. XIO N9:21/3 XIO N9:21/2 MOV 0 N9:43

26. XIC N9:21/10 GRT N9:43 N10:39 BST XIO T4:71/DN TON T4:71 1.0 5 0 NXB XIC T4:71/DN BST ADD N9:73 200 N9:73 NXB GRT N9:73 10000 MOV 10000 N9:73 BND NXB BST EQU N9:107 10000 NXB XIC N9:18/8 BND XIO B3:0/1 BST TON T4:72 1.0 300 0 NXB XIC T4:72/DN OTE N9:18/8 BND BND

27. EQU N10:39 0 MOV 25 N10:39

28. NEQ N9:26 N9:40 BST XIC N9:21/3 GEQ N9:26 2 BST CPT F8:1 (((N9:43*N9:73)|N10:39)*0.25)+(N9:73*0.75) NXB LIM 0.0 F8:1 10000.0 MOV F8:1 N9:73 NXB GRT F8:1 10000.0 MOV 10000 N9:73 BND NXB BST MOV N9:43 N9:46 NXB MOV N9:43 N9:84 NXB MOV 0 N9:43 NXB MOV N9:26 N9:40 BND BND

29. BST LES N9:73 N10:40 MOV N10:40 N9:73 NXB GRT N9:73 N10:41 MOV N10:41 N9:73 BND

30. XIO N9:21/2 XIO N9:21/3 XIO I:5.0/10 MOV 0 N9:73

31. BST BST XIC N9:21/2 NXB XIC N9:21/3 NXB XIC I:5.0/10 BND BST TON T4:24 1.0 5 0 NXB BST XIC N9:21/2 NXB XIC N9:21/3 XIC S:4/5 BND OTE O:1.0/5 NXB XIC T4:24/DN OTE N9:21/10 BND NXB BST XIC N9:21/10 NXB XIC N9:21/9 BND XIC I:8.0/7 OTE O:2.0/14 NXB BST XIC T4:24/EN NXB XIC O:3.0/5 BND XIO T4:52/DN BST OTE O:3.0/5 NXB OTE N9:21/5 BND NXB XIO T4:24/EN TON T4:52 1.0 5 5 BND

32. BST XIC I:5.0/11 BST XIC O:2.0/14 OTE N9:91/9 NXB XIO 0:2.0/14 OTE N9:91/10 BND NXB BST XIO I:5.0/10 XIO I:5.0/11 OTE N9:91/11 NXB XIC I:5.0/10 OTE N9:91/12 BND BND

33. BST XIC N9:16/11 NXB XIC N9:16/12 NXB XIC N9:17/4 NXB XIC N9:17/5 BND OTE N9:91/13

34. BST BST XIC N9:21/2 NXB XIC N9:21/3 NXB XIC I:5.0/12 BND BST OTE O:1.0/6 NXB TON T4:46 1.0 5 0 NXB XIC T4:46/DN XIC I:8.0/7 OTE O:2.0/15 BND NXB BST XIC O:1.0/6 NXB XIC O:3.0/6 BND XIO T4:51/DN BST OTE O:3.0/6 NXB OTE N9:21/7 BND NXB XIO 0:1.0/6 TON T4:51 1.0 55 BND

35. BST XIC O:2.0/15 BST MOV N10:70 N9:80 NXB LES N9:80 N10:42 MOV N10:42 N9:80 NXB GRT N9:80 N10:43 MOV N10:43 N9:80 BND NXB XIO 0:2.0/15 MOV 0 N9:80 BND

36. BST XIC I:5.0/13 BST XIC O:2.0/15 OTE N9:91/14 NXB XIO 0:2.0/15 OTE N9:91/15 BND NXB BST XIO I:5.0/12 XIO I:5.0/13 OTE N9:92/0 NXB XIC I:5.0/12 OTE N9:92/1 BND BND

37. BST XIC N9:16/11 NXB XIC N9:16/12 NXB XIC N9:17/4 NXB XIC N9:17/5 BND OTE N9:92/2

38. BST XIC I:7.0/7 NXB XIO I:7.0/7 XIC B3:0/0 BND OSR B3:0/13 BST ADD N9:66 2 N9:66 NXB DIV N9:66 6 N9:67 BND

39. BST XIC I:5.0/8 NXB XIC I:5.0/9 LES N9:66 2 BND XIO N9:21/2 XIO N9:21/3 XIC N9:21/9 MOV N10:47 N9:107

40. GRT N9:107 0 XIC T4:13/DN ADD N9:68 1 N9:68

41. XIC N9:21/9 GRT N9:81 0 GRT N9:68 N10:37 BST XIO T4:69/DN TON T4:69 1.0 5 0 NXB XIC T4:69/DN BST ADD N9:107 200 N9:107 NXB GRT N9:107 10000 MOV 10000 N9:107 BND NXB BST EQU N9:107 10000 NXB XIC N9:18/7 BND XIO B3:0/1 BST TON T4:70 1.0 300 0 NXB XIC T4:70/DN OTE N9:18/7 BND BND

42. EQU N10:37 0 MOV 50 N10:37

43. XIC I:5.0/9 XIO N9:21/2 XIO N9:21/3 NEQ N9:66 N9:79 BST GEQ N9:66 2 BST CPT F8:2(((N9:68*N9:107)|N10:37)*0.05)+(N9:107*0.95) NXB LIM 0.0 F8:2 10000.0 MOV F8:2 N9107 NXB GRT F8:2 10000.0 MOV 10000 N9:107 BND NXB BST MOV N9:66 N9:79 NXB MOV N9:68 N9:85 NXB MOV 0 N9:68 BND BND

44. XIO N9:17/0 OTE B3:0/15

45. BST LES N9:107 N10:101 MOV N10:101 N9:107 NXB GRT N9:107 N10:102 MOV N10:102 N9:107 BND

46. BST XIC N9:21/2 NXB XIC N9:21/3 NXB XIO I:5.0/8 XIO I:5.0/9 NXB XIO B3:0/15 BND BST MOV 0 N9:107 NXB MOV 0 N9:66 BND

47. BST BST XIC I:5.0/8 NXB XIC I:5.0/9 BND XIO N9:21/2 XIO N9:21/3 XIO N9:91/13 XIO N9:21/10 BST BST XIC I:5.0/9 XIO N10:0/6 NXB XIC I:5.0/8 NXB XIC I:5.0/9 XIC N10:0/6 XIO T4:79/DN BND BST OTE O:1.0/4 NXB OTE N9:21/9 BND NXB XIC I:5.0/9 XIC N10:0/6 XIO T4:80/DN TON T4:79 1.0 119 0 NXB XIC T4:79/DN TON T4:80 1.0 1680 0 BND NXB MOV N10:113 T4:79.PRE NXB MOV N10:1 14 T4:80.PRE BND

48. BST BST XIC I:5.0/8 NXB XIC I:5.0/9 BND XIO N9:21/2 XIO N9:21/3 XIO N9:91/13 XIO N9:21/10 BST BST XIC I:5.0/9 XIC N9:21/14 NXB XIC I:5.0/9 XIO N9:21/14 XIC N10:0/6 XIO T4:79/DN NXB XIC I:5.0/9 XIO N9:21/14 XIO N10:0/6 NXB XIC I:5.0/8 BND BST OTE O:1.0/4 NXB OTE N9:21/9 BND NXB XIC I:5.0/9 XIC N1 0:0/6 XIO T4:80/DN TON T4:79 1.0 119 0 NXB XIC

T4:79/DN TON T4:80 1.0 1680 0 BND NXB MOV N10:1 13 T4:79.PRE NXB MOV N10:114 T4:80.PRE BND

49. XIC N9:21/9 BST GRT N9:81 0 MOV N9:107 N9:73 NXB EQU N9:81 0 MOV N10:105 N9:73 NXB OTE O:3.0/4 BND

50. BST XIC I:5.0/9 BST XIC N9:21/9 OTE N9:91/4 NXB XIO N9:21/9 OTE N9:91/5 BND NXB BST XIO I:5.0/8 XIO I:5.0/9 OTE N9:91/6 NXB XIC I:5.0/8 OTE N9:91/7 BND BND

51. XIC N9:18/7 OTE N9:91/8

Organic Biomass Input Feed Stream

An estimated scope of patent protection that could be reasonably sought for a generic treatment process might be couched as follows:

a) Solid or dry material storage to feed an equalization tank;
b) an equalization (stabilization or mass sedimentation) tank;
c) feed from the equalization tank to an anaerobic digester;
d) flow from the digester to a gas separation zone; and
e) discharge of treated water from the gas separation zone wherein {specific parameters} are sensed in the anaerobic digester to provide signals to a processor that controls influx of i) nutrients, ii) oxidizing agents, inclusive of sulfur and oxygen, iii) antifoam agents and iv) metal additives, wherein with respect to at least two of i), ii), iii) and iv), at least one different condition is sensed to provide sensed data for controlling introduction rates for each of the at least two of i), ii), iii) and iv).

The process may be broadened so as not to require all four additions, with otherwise similar limitations on process control.

Waste food materials may be dry, a slurry, or aqueous in nature. Materials can be stored in segregated fashion, such as individual tanks, or multiple materials can be combined in a single container. Once the material is received and stored, the system can monitor multiple parameters from each storage vessel for each type of waste. While several parameters are common to all types of wastes, some parameters are more appropriate for specific types of wastes. For example, weight is a more appropriate quantitative measure of a dry material while gallons is a more appropriate quantitative measure of an aqueous material. COD is an example of a parameter common to all food wastes.

To maintain the digestion conversion process as close to a theoretical optimal level as possible requires quantitative and qualitative characteristics of the waste materials to be sent to the PLC allowing the PLC to determine the appropriate next step(s) in the process.

Maintaining a relatively stable and consistent organic loading to the digestion step of the process is a critical factor. Waste food material must be processed in various ways depending of the characteristics of the material to form a relatively stable feedstock. Multiple steps may be required. For example, dry material may be required to be ground into smaller particles size and combined with aqueous and/or slurried materials in a proportional manner that creates a feed substrate matching the parameters required by the digestion step of the process. Another example would be that various aqueous materials need to be combined in proportion based on their COD concentrations to result in a COD of the combined material equal or near equal to the desired COD concentration the digester expects to process. A third example would be that the materials lack specific compounds or chemicals such as nitrogen and phosphorus which must be added to the waste material to properly condition the material for digestion. The PLC software can obtain quantitative and qualitative information regarding each type of waste food material and direct the subsequent process steps required to create the desired feed substrate to the digester.

Multiple quantitative and qualitative characteristics are incorporated into the material handing process including:

1. Weight/Volume/Density/Flow
   a. There are many examples of quantitative information that may be used to determine amount of materials available to be processed or being processed. They may be measured at various points along the system, correlated with known or expected results, and the system designed (e.g., programmed or set to provide an alarm or notice) according to past measurements.
2. Viscosity/Moisture content/FOG (Fats, Oils, and Greases)
   a. These are used to determine additional processing requirements such as dilution, from which established needs of the system can be responded to.
   b. These may also be used to determine what type of conveyance device is used to transport the material through additional processing step.
3. pH and alkalinity monitoring and control
   a. Used to determine if the pH must be adjusted. The digestion step in the process operates at neutral pH. Materials being feed to the digestion step should be relatively close to neutral pH to avoid upsetting the digestion process, and/or stores of materials to adjust the pH may be provided in the system, or sources of materials may be adjusted to modify the pH in the desired direction. For example, the pH of two distinct stored organic material sources will have been measured, and the balance of the materials may be shifted to reflect the needs of Ph adjustment suggested by the readings.
4. Temperature
   a. The digestion step requires operating temperatures between 90- and 100 degrees F. for mesophilic operation and between 135 and 150 degrees F. for thermophilic operation. The temperature may be automatically adjusted in response to the measurement of shifting or undesirable temperatures. Waste gases, such as methane may provide energy to heat (by burning) the system or cool the system (by powering a refrigeration unit).
5. BOD/COD/Volatile Acid concentration/Protein concentration/FOG concentration/Carbohydrate concentration/Sugar concentration/Methane potential
   a. These all are examples of parameters which may be used by the PLC to determine proportional amounts of each waste food material required to create the desired feedstock for the digestion step
   b. These are all are examples of parameters which may be used by the PLC in determining if additional compounds or chemicals such as traces metals (nickel, iron, cobalt, etc) are required to be added to the materials when creating the feedstock for the digestion process.
6. Particle Size
   a. Used to determine if waste material should be processed differently though grinding and crushing operations to create the desired particle size/shape in the feedstock for the digestion step. Upon determination of required size change, the operating parameters of material sizing equipment may be altered.

7. Detection of contaminants and alarm
   a. Detection in the raw waste food material of contaminates which would disrupt and/or destroy the biological digestion activity can be essential, and rapid response is desirable. Examples of contaminants include high chlorine levels, and quaternary ammonium. The PLC would not use the contaminated material when creating feedstock for the digestion step of the process. Materials can be available that are known antagonistic vectors against such contaminants and which might leach, absorb, chelate or otherwise restrain or remove such contaminants.
8. General water quality parameters such as conductivity and ORP may also be usefully measured and automatically adjusted in the system.

Energy control, energy output and energy conservation considerations may also be effected and maintained in the operation of the present system. For example, Connections to Energy Production equipment require monitoring and control of equipment. Monitoring and control is done both to optimize energy production and to accurately count the units being sold to the end user.

Parameters controlled by the PLC to optimize energy production are gas input flow maintenance including control valves to supplement with pipeline natural gas as needed to supplement digester gas output. Maintenance of gas blowers to maintain a constant gas pressure, control of equipment for moisture reduction, control of equipment for sulfur dioxide reduction are also required.

Connections to the end-user require connections to, control and measurement of the output electrical power; connections to, control and measurement of hot water piping flows, pressure and hot water heat output; connections to, control and measurement of steam piping, pressure, flow, steam quality and steam heat output.

Figure 1:
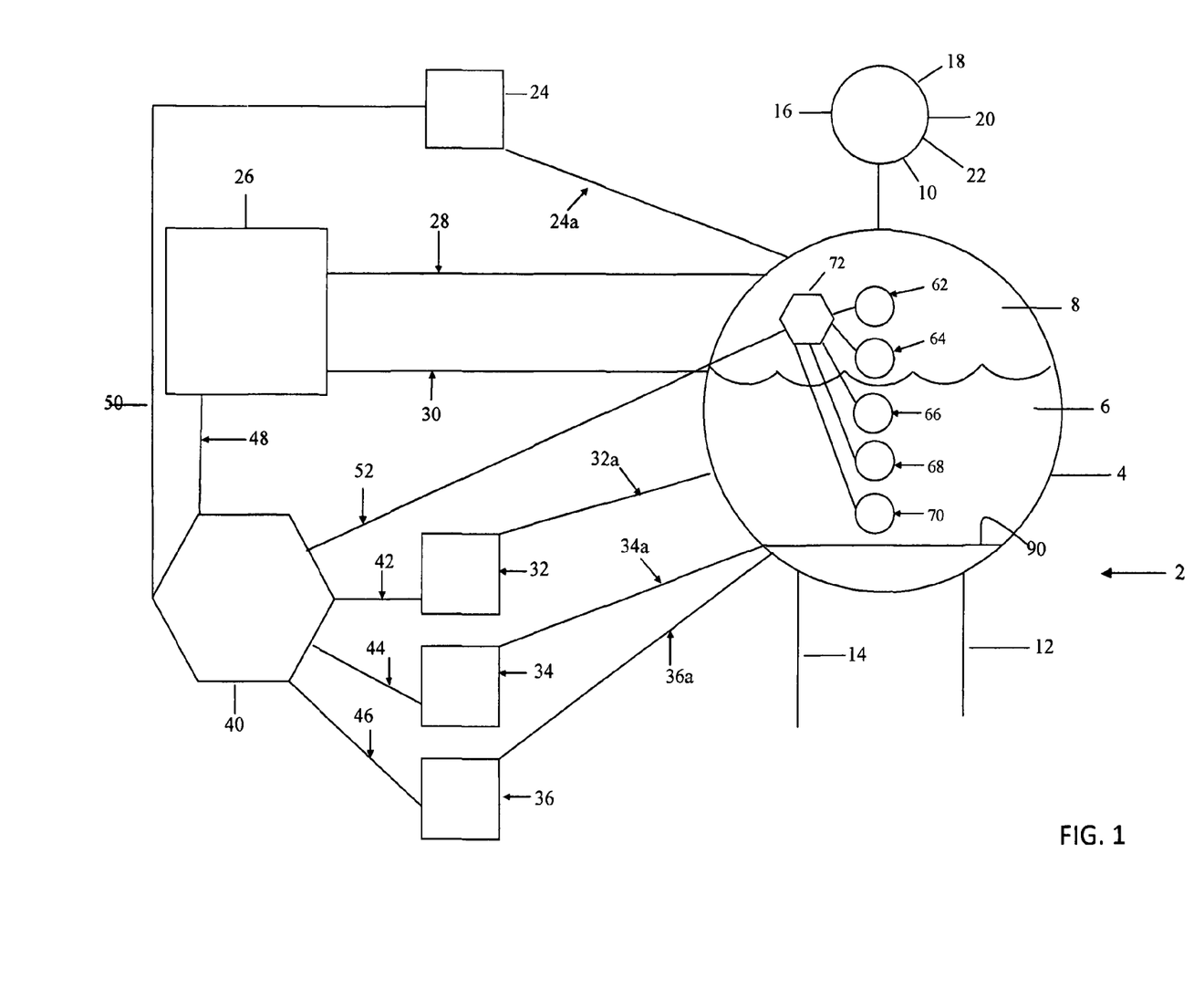
FIG. 1 shows a schematic of a basic biomass decomposition system according to teachings herein.

A view of the Figures will assist in an additional appreciation of the scope of the present technology. FIG. 1 shows a schematic of a basic biomass decomposition system 2 according to teachings herein. The system 2 shown in FIG. 1 has a biomass treatment tank 4 containing the mixture 6 of biomass and liquid and a gas containing space 8 over the mixture 6. The treatment tank 4 is shown with three outlet systems 10, 12 and 14 for the gas outlet (10), the liquid and dissolved, dispersed, suspended solids outlet (12), and an optional mass outlet (12) which may be used for the infrequent removal of excess biomass from the treatment tank 4. The gas outlet 10 is in mass transfer communication with a gas separation system 16, which is shown with three venting outlets 18 (e.g., for $CO_2$), 20 (e.g., for $CH_4$) and residual gas outlet 22 for any other gases emitted. There may be additional vents if $H_2$ is a significant gaseous component of the stream initially vented through outlet 10 from the treatment tank 4.

The configuration of the system 2 in FIG. 1 shows an adjacent organic waste producing commercial facility 26 (e.g., a food processing plant, pharmaceutical plant, or bakery, etc.) that produces both a solids waste stream 28 and an aqueous waste stream 30 that may be fed into the treatment tank as at least one source of both organic solids and aqueous material (which may also contain dissolved, suspended or dispersed solids). The system 2 is also shown with a nutrient storage tank 24 and feed stream 24a to the storage tank 4, and three separate organic solids material storage tanks 32, 34 and 36 with their individual feed streams 32a, 34a and 36a to the treatment tank 4. There may be, and preferably is, a separate aqueous supply stream that can be fed either directly into the treatment tank 4 or into the individual organic solids storage tanks 32, 34 and 36 or into their individual feed streams 32a, 34a and 36a to the treatment tank 4. A central data processing system 40 is shown with various communication links (which may be hard wire or wireless) 52, 42, 44, 46, 48 and 50 to other components (e.g., distal node, FPGA, subprocessor, or signal router 72; organic solid material storage tanks 32, 34 and 36; commercial plant 26; and nutrient storage tank 24, respectively). Each feed stream (including at the site of the storage tank or originating facility) would preferably have an automatically controlled rate flow system in communication link with the central processor 40. A filter bed 90 is shown between the biomass and the liquid outlet 12 to assure retention of larger size particles and other solids.

As indicated more thoroughly in the discussion above, the sensors may be (in the gas volume) for gas pressure, gas temperature, gas content (e.g., methane, carbon dioxide, volatile acid and/or hydrogen content), gas acidity, gas conductivity (as an indication of gas content) and the like, and in the biomass volume for pH, nutrient content, temperature, density, temperature, specific component or by-product content, water content, chemical oxygen concentration or requirements, flow rates through the filter or into the liquid outlet 12, and the like, as described above.

Inside and/or at flow inlets and outlets to the treatment tank 4 may be sensors as indicated in the discussion above. In FIG. 1 are shown two sensors 62 and 64 in the gas volume 8 in the treatment tank 4 and three sensors 66, 68 and 70 in the biomass volume 6 in the treatment tank 4. These sensors 62, 64, 66, 68 and 70 may be in direct communication with the processor 40 or may be linked to the processor 40 through a router or other intermediary device 72. In order to reduce computing power needed and to simplify repair and replacement of parts, the sensors may communicate as nodes in a distributed architecture format, using linking element 72 to properly format, translate or encode signals to be sent to processor 40 for reading, storage and analysis, followed by commands or state change signals from the processor or responsive or controlled elements, such as the flow control or rate of flow control in the various sources of materials (and energy) to the treatment tank 4, as explained above.

Attached and incorporated into this application is Appendix I, which contains three distinct software ladders for use in various individual and separate component sequences in the practice of technology that is described herein. LAD 6 represents a sequence that may be used with the digester discharge controls and constitutes copyrighted code and material of the assignee.

LAD 5 represents a sequence that may be used with the digester agitator controls and constitutes copyrighted code and material of the assignee.

LAD 11 represents a sequence that may be used with the Titrator Sequence controls and constitutes copyrighted code and material of the assignee.

Other software for other individual performance steps identified in this disclosure may be similarly structured as taught by the technology. One of ordinary skill in the art, upon reading this disclosure will become readily aware of variations, alternatives and orientations that are not specifically identified in this disclosure, but which are within the scope of the technology disclosed. These variations and equivalents are intended to be included within this disclosure and the discussion of specific structures, materials, software and line code is not intended to limit the scope of protection afforded by the following claims to this technology.

The attached Appendix I is incorporated by reference in their entirety herein.

All references to other publications mentioned in this patent specification are hereby incorporated by reference in their entirety as if fully set forth herein.

What is claimed:

1. A method of decomposition of organic waste material comprising:
providing a treatment tank for decomposition of organic waste material, the treatment tank containing an active biomass comprising at least one bacteria that decomposes organic material;
providing at least two inlets to the treatment tank, a first inlet comprising an inlet for an at least one first organic material and a second inlet comprising an inlet for an aqueous stream;
receiving and storing information on a processor receiving, said information comprising:
the status of chemical oxygen demand in the treatment tank; and
the oxygen demand of the first at least one organic material that can be fed into the treatment tank through the first inlet;
feeding the at least one first organic material through the first inlet into the treatment tank;
feeding an aqueous stream through the second inlet into the treatment tank;
controlling a mass flow control system with a processor to feed the at least one organic material through the first inlet at an introduction rate; and
altering the introduction rate of the at least one first organic material based at least in part upon the status of chemical oxygen demand in the treatment tank as recognized by the processor.

2. The method of claim 1 wherein there are at least two storage tanks for organic material, a first storage tank for the first organic material and a second storage tank for a second organic material, the first and second organic materials having different chemical oxygen provision capabilities from each other;
the processor receiving and storing information on the respective chemical oxygen provision capabilities of the first organic material and the second organic material; and
the processor controlling feeding of at least one of the first organic material and the second organic material into the treatment tank at a rate based at least in part upon the status of chemical oxygen demand in the treatment tank, the chemical oxygen provision capability of the first organic material, and the chemical oxygen provision capability of the second organic material as recognized by the processor; and
filtering a stream of material with a filter present between the active biomass in the treatment tank and the treated aqueous outlet.

3. The method of claim 1 wherein a treated aqueous stream is removed from the treatment tank through an aqueous stream outlet and a gas decomposition stream through a gas venting outlet, the gas decomposition stream comprising methane and carbon dioxide is removed from the treatment tank.

4. The method of claim 3 wherein at least one of the active biomass and treated aqueous stream are automatically tested for active biomass nutrient content and testing information is provided to the processor.

5. The method of claim 4 wherein testing is performed for active biomass nutrient content and when testing for active biomass nutrient content indicates that the nutrient level in the treatment tank is not within a predetermined desired range, the processor directs a nutrient feed system to input nutrient material into the treatment tank to bring nutrient level in the tank within the predetermined desired range.

6. The method of claim 3 wherein testing is performed for pH and when testing for pH indicates that the pH level in the treatment tank is not within a predetermined desired range, a feed system for a pH active material selected from the class consisting of at least one of a base, an acid or a buffer to input pH active material into the treatment tank is directed to bring the pH level in the tank within the desired range.

7. The method of claim 5 wherein testing is performed for at least one of available nitrogen and available phosphorus, and the results of such testing are used by the processor to determine how much nutrient is to be added to the treatment tank to specifically adjust at least one of nitrogen and phosphorus content in the treatment tank.

8. The method of claim 1 wherein mass flow through the system is at least in part automatically controlled by sensing at least one of a) weight; b) Viscosity; c) pH; d) Temperature; e) Particle Size; f) Detection of contaminants and alarm upon detection of contaminants; g) water quality parameters, h) Protein concentration and i) Methane potential and automatically providing a response to the sensing according to at least one of a lookup table, hardware response and software response.

9. The method of claim 1 wherein the treatment tank is sensed and automatically responded to by sensing at least one condition selected from the group consisting of a) Contaminant alarm; b) Solids concentration monitoring and control; c) BOD and COD monitoring and control; d) surface tension; e) foam detection; f) Dissolved gas monitoring; g) Volatile acids monitoring; h) Detection of specific bacteria concentration; i) fat monitoring; j) grease monitoring; and k) oil monitoring; and the processor automatically responds thereto.

10. A method of decomposing of organic waste material comprising:
providing a treatment tank for decomposition of organic waste material, the treatment tank containing an active biomass comprising at least one bacteria that decomposes organic material;
providing at least two inlets to the treatment tank, a first inlet comprising an inlet for organic material and a second inlet comprising an inlet for an aqueous stream;
a processor receiving and stores information on:
the status of chemical oxygen demand for the tank;
the oxygen provision capability of materials in and into the treatment tank;
the processor controlling a mass flow control system to feed at least one organic material through the first inlet at a rate based at least in part upon the status of chemical oxygen demand in the treatment tank as recognized by the processor; and
decomposing the at least one organic material with the biomass.

11. The method of claim 10 wherein a treated aqueous stream is removed from the treatment tank through an aqueous stream outlet and a gas decomposition stream through a gas venting outlet, the gas decomposition stream comprising methane.

12. The method of claim 11 wherein at least one of the active biomass and treated aqueous stream are automatically tested for active biomass nutrient content and testing information for the active biomass nutrient content is provided to the processor.

* * * * *